(12) United States Patent
Jeong et al.

(10) Patent No.: US 11,585,700 B2
(45) Date of Patent: Feb. 21, 2023

(54) STRETCHABLE SENSOR FOR SENSING MULTIMODAL TEMPERATURE AND STRAIN

(71) Applicants: POSTECH Research and Business Development Foundation, Pohang-si (KR); THE BOARD OF TRUSTEES OF THE LELAND STANFORD JUNIOR UNIVERSITY, Stanford, CA (US)

(72) Inventors: Unyong Jeong, Pohang-si (KR); Insang You, Pohang-si (KR); Zhenan Bao, Stanford, CA (US)

(73) Assignees: POSTECH RESEARCH AND BUSINESS DEVELOPMENT FOUNDATION, Pohang-si (KR); THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 32 days.

(21) Appl. No.: 17/109,232

(22) Filed: Dec. 2, 2020

(65) Prior Publication Data
US 2022/0170797 A1 Jun. 2, 2022

(51) Int. Cl.
*G01L 1/22* (2006.01)
*G01K 1/26* (2006.01)
(Continued)

(52) U.S. Cl.
CPC ............... *G01K 1/26* (2013.01); *A61F 2/105* (2013.01); *G01L 1/2281* (2013.01); *G01L 5/0038* (2013.01)

(58) Field of Classification Search
None
See application file for complete search history.

(56) References Cited

U.S. PATENT DOCUMENTS 4,600,855 A * 7/1986 Strachan ............... G01L 1/162
73/702
9,697,959 B2 * 7/2017 Anderson ............ H03K 17/965

FOREIGN PATENT DOCUMENTS

KR         101876438       7/2018
KR    10-2019-0011431      2/2019
(Continued)

OTHER PUBLICATIONS

Insang You, "Morphology Design and Impedance Analysis of Composite Materials for Signal Decoupling in Deformable Sensors" Doctoral Thesis of inventor, Deparlment of Materials Science and Engineering, Pohang University of Science and Technology, Mar. 31, 2020.
(Continued)

*Primary Examiner* — Lisa M Caputo
*Assistant Examiner* — Nigel H Plumb
(74) *Attorney, Agent, or Firm* — Lex IP Meister, PLLC

(57) ABSTRACT

A stretchable sensor is provided. The stretchable sensor includes a first stretchable electrode including a first elastomer and a first conductor dispersed in the first elastomer, a stretchable active layer formed on the first stretchable electrode and including a third elastomer and an ion conductor dispersed in the third elastomer, and a second stretchable electrode formed on the stretchable active layer and including a second elastomer and a second conductor dispersed in the second elastomer. The stretchable sensor is effectively capable of sensing a temperature without being affected by strain and recognizing strain without being affected by temperature.

16 Claims, 20 Drawing Sheets

(51) Int. Cl.
*A61F 2/10* (2006.01)
*G01L 5/00* (2006.01)

(56) References Cited

FOREIGN PATENT DOCUMENTS

KR  10-2020-0045255  5/2020
KR  10-2020-0020429  2/2022

OTHER PUBLICATIONS

KIP, Office Action of KR 10-2020-0180880 dated Nov. 25, 2022.
Insang You et al., "Artificial multimodal receptors based on ion relaxation dynamics", Science 370, 961-965, Nov. 20, 2020.

* cited by examiner

STRETCHABLE SENSOR FOR SENSING MULTIMODAL TEMPERATURE AND STRAIN

BACKGROUND OF THE DISCLOSURE

1. Technical Field

The present disclosure relates to a stretchable sensor, electronic skin, and a method of manufacturing the same, and more particularly to a stretchable sensor for sensing multimodal temperature and strain, electronic skin, and a method of manufacturing the same.

2. Description of the Related Art

The somatosensory system of the human skin is characterized by several unique properties. The receptors thereof are made up of ion conductors and the operation thereof is based on ionic mechanics.

With reference to FIG. 1A, pluralities of thermoreceptors and mechanoreceptors are spatially distributed in the dermis, and thus the spatial profile of strain and temperature on the skin can be perceived distinctively. With reference to FIG. 1B, the mechanical deformability of the ion receptor enables signal stability to be maintained under large shear strain. Depending on the viscoelasticity of the skin, various stimuli, such as pressing, shearing, pinching, torsion and combinations thereof, form 3-dimensional (3D) deformation and are visualized by wrinkle formation. The skin has local distributions of regions of contact and strain, for example, wrinkles are seen in compressed regions of skin while the regions of the other side are stretched based on the contacted region.

Temperature sensing is essential for monitoring physiological changes in the body, and is an important element of tactile sensation. Since the combination of 3D deformations creates a complex stress field, real-time acquisition of the spatial profile of contact and strain is necessary to understand the perception of the skin sensory system.

Electronic skin (E-skin) aims to mimic human somatosensory functions. E-skin is expected to play an important role as an alternative to actual skin or as a sensing/actuation interface in virtual reality. This has demonstrated potential applicability in haptic devices, wearable healthcare sensors, prosthetics, artificial electronic skin for robots, and implantable medical devices. However, despite the remarkable advances thereof, manufacturing multifunctional E-skin is still a big challenge. Research has been carried out to sense multiple stimuli by integrating several types of sensors, but there is a problem in that it is difficult to realize integration due to structural complexity.

SUMMARY OF THE DISCLOSURE

Accordingly, the present disclosure has been made keeping in mind the problems encountered in the related art, and an objective of the present disclosure is to provide a stretchable sensor capable of sensing a temperature without being affected by strain and recognizing strain without being affected by temperature, and a method of manufacturing the same.

An aspect of the present disclosure provides a stretchable sensor 10, including: a first stretchable electrode 100 including a first elastomer and a first conductor dispersed in the first elastomer; a stretchable active layer 200 formed on the first stretchable electrode 100 and including a third elastomer and an ion conductor dispersed in the third elastomer; and a second stretchable electrode 300 formed on the stretchable active layer 200 and including a second elastomer and a second conductor dispersed in the second elastomer.

Also, the stretchable active layer 200 may be electrically connected to each of the first stretchable electrode 100 and the second stretchable electrode 300.

Also, all or a portion of the ion conductor may come into contact with all or a portion of the first conductor at an interface between the stretchable active layer 200 and the first stretchable electrode 100, and all or a portion of the ion conductor may come into contact with all or a portion of the second conductor at an interface between the stretchable active layer 200 and the second stretchable electrode 300.

Also, the stretchable sensor 10 may further include a first stretchable substrate 400 located on the first stretchable electrode 100 in a direction opposite a direction facing the stretchable active layer 200 and a second stretchable substrate 500 located on the second stretchable electrode 300 in a direction opposite a direction facing the stretchable active layer 200.

Also, the first conductor and the second conductor may be the same as or different from each other, and each of the first conductor and the second conductor may independently include at least one selected from the group consisting of silver (Ag), gold (Au), platinum (Pt), palladium (Pd), copper (Cu), cobalt (Co), zirconium (Zr), zinc (Zn), titanium (Ti), tin (Sn), and a conductive polymer.

The conductive polymer may be PEDOT:PSS.

Also, each of the first conductor and the second conductor may have a nanowire shape.

Also, each of the first elastomer and the second elastomer may be a thermoplastic elastomer.

Also, the thermoplastic elastomer may include at least one selected from the group consisting of a styrene-ethylene-butylene-styrene (SEBS) block copolymer, a styrene-butadiene-styrene (SBS) block copolymer, a styrene-isoprene-styrene (SIS) block copolymer, thermoplastic polyurethane (PU), polyisoprene rubber (IR), butadiene rubber (BR), and ethylene-propylene-diene monomer (EPDM) rubber.

Also, the third elastomer may be a thermosetting elastomer.

Also, the thermosetting elastomer may include at least one selected from the group consisting of a fluoroelastomer, poly(vinylidene fluoride-co-hexafluoropropylene), thermosetting polyurethane, polydimethylsiloxane (PDMS), silicone rubber, Ecoflex, and Dragon Skin.

Also, the stretchable active layer 200 may include 100 parts by weight of the third elastomer and 0.1 to 50 parts by weight of the ion conductor.

Also, the ion conductor may include an ionic liquid.

Also, the ionic liquid may include at least one selected from the group consisting of an aliphatic ionic liquid, an imidazolium-based ionic liquid, and a pyridinium-based ionic liquid.

Also, the first stretchable electrode 100 may include a plurality of first electrodes 110 parallel to each other in a linear arrangement, the second stretchable electrode 300 may include a plurality of second electrodes 310 parallel to each other in a linear arrangement, the first electrodes 110 are located perpendicular to the second electrodes 310, the first electrodes 110 and the second electrodes 310 form a pixel structure, and the stretchable sensor 10 may be used for electronic skin.

Another aspect of the present disclosure provides a method of manufacturing a stretchable sensor 10, including:

(a) manufacturing a first stretchable electrode 100 including a first elastomer and a first conductor dispersed in the first elastomer; (b) manufacturing a bottom layer by forming a stretchable active layer 200 including a third elastomer and an ion conductor dispersed in the third elastomer on the first stretchable electrode 100; (c) manufacturing a second stretchable electrode 300 including a second elastomer and a second conductor dispersed in the second elastomer; (d) manufacturing a top layer by forming a stretchable active layer 200 including a third elastomer and an ion conductor dispersed in the third elastomer on the second stretchable electrode 300; and (e) disposing the stretchable active layer 200 of the bottom layer and the stretchable active layer 200 of the top layer to be in contact with each other.

Also, the method may further include, after step (e), (f) crosslinking the stretchable active layers 200 disposed to be in contact with each other in step (e).

Also, step (a) may include (a-1) forming a first conductor coating layer on a substrate by performing coating with a first conductor solution including a first conductor on the substrate and performing drying and (a-2) manufacturing a first stretchable electrode 100 including the first conductor dispersed in a first elastomer by performing coating with a first elastomer solution including the first elastomer on the first conductor coating layer and performing drying.

Also, step (c) may include (c-1) forming a second conductor coating layer on a substrate by performing coating with a second conductor solution including a second conductor on the substrate and performing drying and (c-2) manufacturing a second stretchable electrode 300 including the second conductor dispersed in a second elastomer by performing coating with a second elastomer solution including the second elastomer on the second conductor coating layer and performing drying.

Still another aspect of the present disclosure provides a method of sensing a temperature using a stretchable sensor 10 including a stretchable active layer 200 including an elastomer and an ion conductor dispersed in the elastomer, including: (1) measuring respective impedances $Z_1$ and $Z_2$ at two arbitrary frequencies $\omega_1$ and $\omega_2$ ($\omega_1 < \omega_2$); (2) determining a resistance R, which is the real impedance $Z_{re}$, from the impedance $Z_1$; (3) determining an imaginary impedance $Z_{im}$ from the impedance $Z_2$ and substituting the imaginary impedance $Z_{im}$ into Equation 1 below to obtain a capacitance C; (4) substituting the resistance R and the capacitance C into Equation 2 below to obtain a relaxation time τ; and (5) determining a temperature using the relaxation time τ.

$$Z_{im} = \frac{1}{\omega_i C} \qquad \text{[Equation 1]}$$

$$\tau = RC \qquad \text{[Equation 2]}$$

In Equations 1 and 2, $Z_{im}$ is the imaginary impedance, ω is the frequency, i is 1 or 2, C is the capacitance, τ is the relaxation time, and R is the resistance.

Also, the real impedance may be measured at a frequency ranging from $0.001 \times 10^3$ Hz to $1.0 \times 10^3$ Hz.

Also, the imaginary impedance may be measured at a frequency ranging from $0.001 \times 10^7$ Hz to $1.0 \times 10^7$ Hz.

Yet another aspect of the present disclosure provides a method of sensing strain using a stretchable sensor 10 including a stretchable active layer 200 including an elastomer and an ion conductor dispersed in the elastomer, including: (1') measuring respective impedances $Z_1$ and $Z_2$ at two arbitrary frequencies $\omega_1$ and $\omega_2$ ($\omega_1 < \omega_2$); (2') determining a resistance R, which is the real impedance $Z_{re}$, from the impedance $Z_1$; (3') determining an imaginary impedance $Z_{im}$ from the impedance $Z_2$ and substituting the imaginary impedance $Z_{im}$ into Equation 1 below to obtain a capacitance C; (4') substituting the resistance R and the capacitance C into Equation 2 below to obtain a relaxation time τ; (5') determining a capacitance $C_0$ in a non-strained state using the relaxation time τ; and (6') determining a strain using the capacitance C and the capacitance $C_0$ in the non-strained state.

$$Z_{im} = \frac{1}{\omega_i C} \qquad \text{[Equation 1]}$$

$$\tau = RC \qquad \text{[Equation 2]}$$

In Equations 1 and 2, $Z_{im}$ is the imaginary impedance, ω is the frequency, i is 1 or 2, C is the capacitance, τ is the relaxation time, and R is the resistance.

According to the present disclosure, a stretchable sensor and a method of manufacturing the same are effectively capable of sensing a temperature without being affected by strain and recognizing strain without being affected by temperature.

DESCRIPTION OF SPECIFIC EMBODIMENTS

The present disclosure may be embodied in many different forms, and should not be construed as being limited only to the embodiments set forth herein, but should be understood to cover all modifications, equivalents or alternatives falling within the spirit and technical scope of the present disclosure. In the description of the present disclosure, detailed descriptions of related known techniques incorporated herein will be omitted when the same may make the gist of the present disclosure unclear.

As used herein, the terms "first", "second", etc. may be used to describe various elements, but these elements are not to be limited by these terms. These terms are only used to distinguish one element from another. For example, a first element may be termed a second element, and similarly, a second element may be termed a first element, without departing from the scope of the present disclosure.

Further, it will be understood that when an element is referred to as being "formed" or "stacked" on another element, it can be formed or stacked so as to be directly attached to all surfaces or one surface of the other element, or intervening elements may be present therebetween.

Unless otherwise stated, the singular expression includes a plural expression. In this application, the terms "comprise", "include" or "have" are used to designate the presence of features, numbers, steps, operations, elements, parts, or combinations thereof described in the specification, and should be understood as not excluding the presence or additional possible presence of one or more different features, numbers, steps, operations, elements, parts, or combinations thereof.

Figure 2:
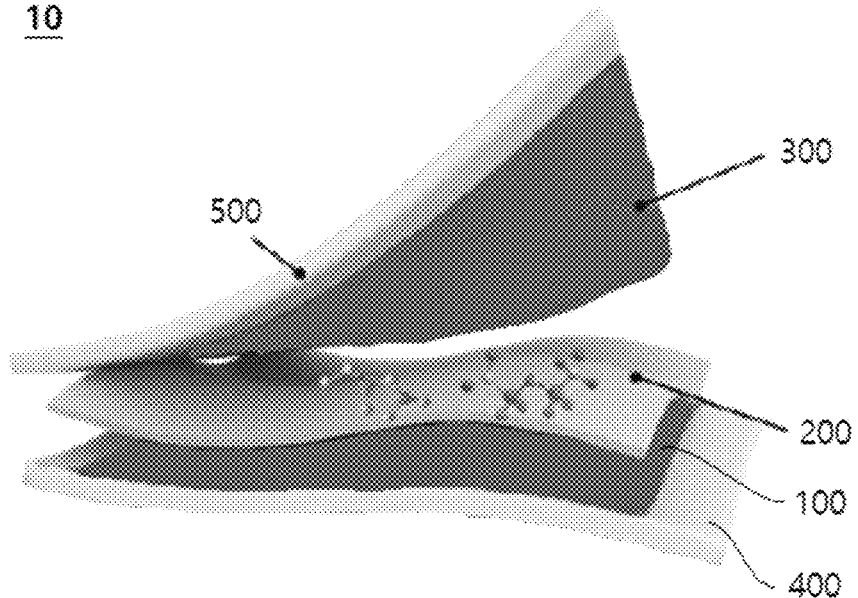
FIG. 2 schematically shows the configuration of a stretchable sensor according to the present disclosure.

FIG. 2 schematically shows the configuration of a stretchable sensor according to the present disclosure. Hereinafter, the stretchable sensor according to the present disclosure is described with reference to FIG. 2.

The present disclosure pertains to a stretchable sensor 10, including: a first stretchable electrode 100 including a first elastomer and a first conductor dispersed in the first elastomer; a stretchable active layer 200 formed on the first stretchable electrode 100 and including a third elastomer and an ion conductor dispersed in the third elastomer; and a second stretchable electrode 300 formed on the stretchable active layer 200 and including a second elastomer and a second conductor dispersed in the second elastomer.

The stretchable active layer 200 may be electrically connected to each of the first stretchable electrode 100 and the second stretchable electrode 300.

All or a portion of the ion conductor may come into contact with all or a portion of the first conductor at the interface between the stretchable active layer 200 and the first stretchable electrode 100, and all or a portion of the ion conductor may come into contact with all or a portion of the second conductor at the interface between the stretchable active layer 200 and the second stretchable electrode 300.

The stretchable sensor 10 may further include a first stretchable substrate 400, located on the first stretchable electrode 100 in a direction opposite the direction facing the stretchable active layer 200, and a second stretchable substrate 500, located on the second stretchable electrode 300 in a direction opposite the direction facing the stretchable active layer 200.

The first conductor and the second conductor may be the same as or different from each other, and each of the first conductor and the second conductor may independently include at least one selected from the group consisting of silver (Ag), gold (Au), platinum (Pt), palladium (Pd), copper (Cu), cobalt (Co), zirconium (Zr), zinc (Zn), titanium (Ti), tin (Sn), and a conductive polymer.

The conductive polymer may be PEDOT:PSS.

Each of the first conductor and the second conductor may have a nanowire shape.

Each of the first elastomer and the second elastomer may be a thermoplastic elastomer.

The thermoplastic elastomer may include at least one selected from the group consisting of a styrene-ethylene-butylene-styrene (SEBS) block copolymer, a styrene-butadiene-styrene (SBS) block copolymer, a styrene-isoprene-styrene (SIS) block copolymer, thermoplastic polyurethane (PU), polyisoprene rubber (IR), butadiene rubber (BR), and ethylene-propylene-diene monomer (EPDM) rubber.

The third elastomer may be a thermosetting elastomer.

The thermosetting elastomer may include at least one selected from the group consisting of a fluoroelastomer, poly(vinylidene fluoride-co-hexafluoropropylene), thermosetting polyurethane, polydimethylsiloxane (PDMS), silicone rubber, Ecoflex, and Dragon Skin.

The stretchable active layer 200 may include 100 parts by weight of the third elastomer and 0.1 to 50 parts by weight of the ion conductor.

The ion conductor may include an ionic liquid.

The ionic liquid may include at least one selected from the group consisting of an aliphatic ionic liquid, an imidazolium-based ionic liquid, and a pyridinium-based ionic liquid.

The aliphatic ionic liquid may be at least one selected from the group consisting of N,N,N-trimethyl-N-propylammonium bis(trifluoromethanesulfonyl)imide (TMPA-TFSI), N-methyl-N-propyl piperidinium bis(trifluoromethanesulfonyl)imide, N,N-diethyl-N-methyl-N-(2-methoxyethyl)ammonium bis(trifluoromethanesulfonyl)imide, and N,N-diethyl-N-methyl-N-(2-methoxyethyl)ammonium tetrafluoroborate.

The imidazolium-based ionic liquid may be at least one selected from the group consisting of 1-ethyl-3-methylimidazolium bis(trifluoromethylsulfonyl)imide, 1-ethyl-3-methylimidazolium bromide, 1-ethyl-3-methyl-imidazolium chloride, 1-ethyl-3-methylimidazolium (L)-lactate, 1-ethyl-3-methylimidazolium hexafluorophosphate, 1-ethyl-3-methylimidazolium tetrafluoroborate (EMI-BF4), 1-butyl-3-methylimidazolium chloride, 1-butyl-3-methylimidazolium hexafluorophosphate, 1-butyl-3-methylimidazolium tetrafluoroborate (BMI-BF4), 1-butyl-3-methylimidazolium trifluoromethanesulfonate, 1-butyl-3-methylimidazolium (L)-lactate, 1-hexyl-3-methylimidazolium bromide, 1-hexyl-3-methylimidazolium chloride, 1-hexyl-3-methyl-imidazolium hexafluorophosphate, 1-hexyl-3-methylimidazolium tetrafluoroborate, 1-hexyl-3-methylimidazolium trifluoromethane sulfonate, 1-octyl-3-methylimidazolium chloride, 1-octyl-3-methylimidazolium hexafluorophosphate, 1-decyl-3-methylimidazolium chloride, 1-dodecyl-3-methylimidazolium chloride, 1-tetradecyl-3-methylimidazolium chloride, 1-hexadecyl-3-methylimidazolium chloride, 1-octadecyl-3-methylimidazolium chloride, 1-ethyl-2,3-dimethylimidazolium bromide, 1-ethyl-2,3-dimethylimidazolium chloride, 1-butyl-2,3-dimethylimidazolium bromide, 1-butyl-2,3-dimethylimidazolium chloride, 1-butyl-2,3-dimethylimidazolium tetrafluoroborate, 1-butyl-2,3-dimethylimidazolium trifluoromethane sulfonate, 1-hexyl-2,3-dimethylimidazolium bromide, 1-hexyl-2,3-dimethylimidazolium chloride, and 1-hexyl-2,3-dimethylimidazolium trifluoromethane sulfonate.

The pyridinium-based ionic liquid may be at least one selected from the group consisting of 1-ethyl pyridinium bromide, 1-ethyl pyridinium chloride, 1-butyl pyridinium bromide, 1-butyl pyridinium chloride, 1-butyl pyridinium hexafluorophosphate, 1-butyl pyridinium tetrafluoroborate, 1-butyl pyridinium trifluoromethane sulfonate, 1-hexyl pyridinium bromide, 1-hexyl pyridinium chloride, 1-hexyl pyridinium hexafluorophosphate, 1-hexyl pyridinium tetrafluoroborate, and 1-hexyl pyridinium trifluoromethane sulfonate.

The ionic liquid is preferably an imidazolium-based ionic liquid, and the imidazolium-based ionic liquid is preferably 1-ethyl-3-methylimidazolium bis(trifluoromethylsulfonyl)imide (EMIM-TFSI).

The first stretchable electrode 100 includes a plurality of first electrodes 110 parallel to each other in a linear arrangement, and the second stretchable electrode 300 includes a plurality of second electrodes 310 parallel to each other in a linear arrangement. The first electrodes 110 are located perpendicular to the second electrodes 310, the first electrodes 110 and the second electrodes 310 form a pixel structure, and the stretchable sensor 10 may be used for E-skin.

Figure 3:
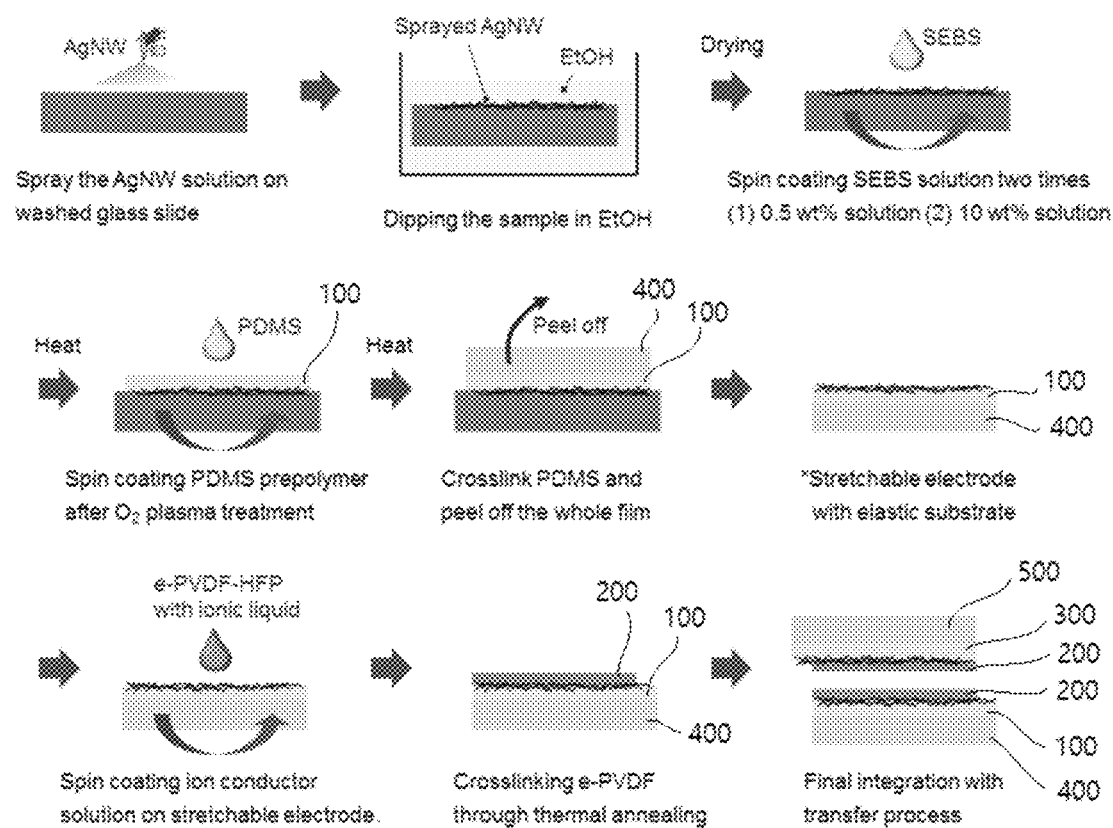
FIG. 3 schematically shows a process of manufacturing the stretchable sensor according to the present disclosure.

FIG. 3 schematically shows the process of manufacturing the stretchable sensor according to the present disclosure. With reference to FIG. 3, the method of manufacturing the stretchable sensor according to the present disclosure is described below.

First, a first stretchable electrode 100 including a first elastomer and a first conductor dispersed in the first elastomer is manufactured (step a).

Step (a) may include (a-1) forming a first conductor coating layer on a substrate by performing coating with a first conductor solution including a first conductor on the substrate and performing drying, and (a-2) manufacturing a first stretchable electrode 100 including the first conductor dispersed in a first elastomer by performing coating with a first elastomer solution including the first elastomer on the first conductor coating layer and performing drying.

Next, a bottom layer is manufactured by forming a stretchable active layer 200 including a third elastomer and an ion conductor dispersed in the third elastomer on the first stretchable electrode 100 (step b).

Subsequently, a second stretchable electrode 300 including a second elastomer and a second conductor dispersed in the second elastomer is manufactured (step c).

Step (c) may include (c-1) forming a second conductor coating layer on a substrate by performing coating with a second conductor solution including a second conductor on the substrate and performing drying, and (c-2) manufacturing a second stretchable electrode 300 including the second conductor dispersed in a second elastomer by performing coating with a second elastomer solution including the second elastomer on the second conductor coating layer and performing drying.

Next, a top layer is manufactured by forming a stretchable active layer 200 including a third elastomer and an ion conductor dispersed in the third elastomer on the second stretchable electrode 300 (step d).

Finally, the stretchable active layer 200 of the bottom layer and the stretchable active layer 200 of the top layer are disposed to be in contact with each other (step e).

After step (e), (f) crosslinking the stretchable active layers 200 disposed to be in contact with each other in step (e) may be further performed.

Below, a method of sensing a temperature using the stretchable sensor 10 according to the present disclosure is described.

First, respective impedances $Z_1$ and $Z_2$ are measured at two arbitrary frequencies $\omega_1$ and $\omega_2$ ($\omega_1 < \omega_2$) (step 1).

Figure 4A:
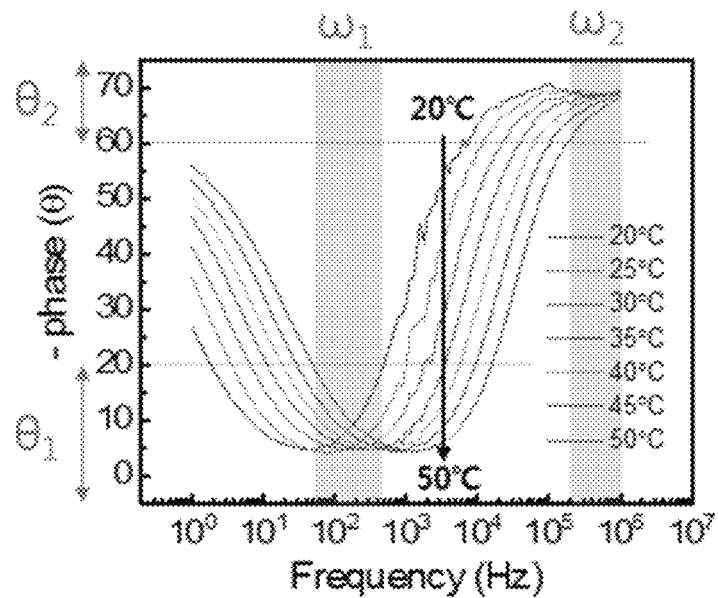
FIG. 4A is a graph showing the phase depending on the frequency at various temperatures (20° C.-50° C.) of the stretchable sensor according to the present disclosure.
Figure 4B:
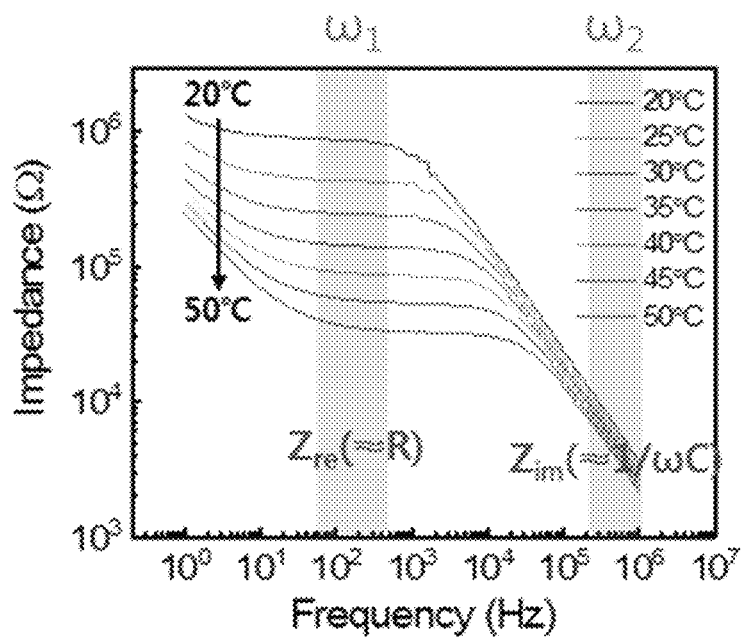
FIG. 4B is a graph showing the impedance depending on the frequency at various temperatures (20° C.-50° C.) of the stretchable sensor according to the present disclosure.

With reference to FIGS. 4A and 4B, the arbitrary frequency region is determined using the phase graph of FIG. 4A, and is applied to the impedance graph of FIG. 4B, thus measuring $Z_1$ and $Z_2$. Specifically, with reference to FIG. 4A, $\omega_1$ is the frequency of the region in which the phase of all Bode plots satisfies $0° < \theta_1 < -20°$ in the target temperature range (the region in which the real impedance is dominant), and $\omega_2$ is the frequency of the region in which the phase of all Bode plots satisfies $-60° < \theta_2 < -90°$ in the target temperature range (the region in which the imaginary impedance is dominant). With reference to FIG. 4B, the impedances $Z_1$ and $Z_2$ are measured from the frequency regions determined above.

Next, a resistance R, which is the real impedance $Z_{re}$, is determined from the impedance $Z_1$ (step 2).

Subsequently, an imaginary impedance $Z_{im}$ is determined from the impedance $Z_2$, and the imaginary impedance $Z_{im}$ is substituted into Equation 1 to obtain a capacitance C (step 3).

$$Z_{im} = \frac{1}{\omega_i C} \quad \text{[Equation 1]}$$

In Equation 1, $Z_{im}$ is the imaginary impedance, ω is the frequency, i is 1 or 2, and C is the capacitance.

Next, a relaxation time τ is determined by substituting the resistance R and the capacitance C into Equation 2 (step 4).

$$\tau = RC \quad \text{[Equation 2]}$$

In Equation 2, τ is the relaxation time and R is the resistance.

Finally, a temperature is determined using the relaxation time τ (step 5).

The real impedance may be measured at a frequency ranging from $0.001 \times 10^3$ Hz to $1.0 \times 10^3$ Hz.

The imaginary impedance may be measured at a frequency ranging from $0.001 \times 10^7$ Hz to $1.0 \times 10^7$ Hz.

Below, a method of sensing strain using the stretchable sensor according to the present disclosure is described.

First, respective impedances $Z_1$ and $Z_2$ are measured at two arbitrary frequencies $\omega_1$ and $\omega_2$ ($\omega_1 < \omega_2$) (step 1').

Next, a resistance R, which is the real impedance $Z_{re}$, is determined from the impedance $Z_1$ (step 2').

Subsequently, an imaginary impedance $Z_{im}$ is determined from the impedance $Z_2$, and the imaginary impedance $Z_{im}$ is substituted into Equation 1 to obtain a capacitance C (step 3').

$$Z_{im} = \frac{1}{\omega_i C} \quad \text{[Equation 1]}$$

In Equation 1, $Z_{im}$ is the imaginary impedance, ω is the frequency, i is 1 or 2, and C is the capacitance.

Next, a relaxation time τ is determined by substituting the resistance R and the capacitance C into Equation 2 (step 4').

$$\tau = RC \quad \text{[Equation 2]}$$

In Equation 2, τ is the relaxation time and R is the resistance.

Next, a capacitance $C_0$ in the non-strained state is determined using the relaxation time τ (step 5').

Finally, strain is determined using the capacitance C and the capacitance $C_0$ in the non-strained state (step 6').

Figure 6A:
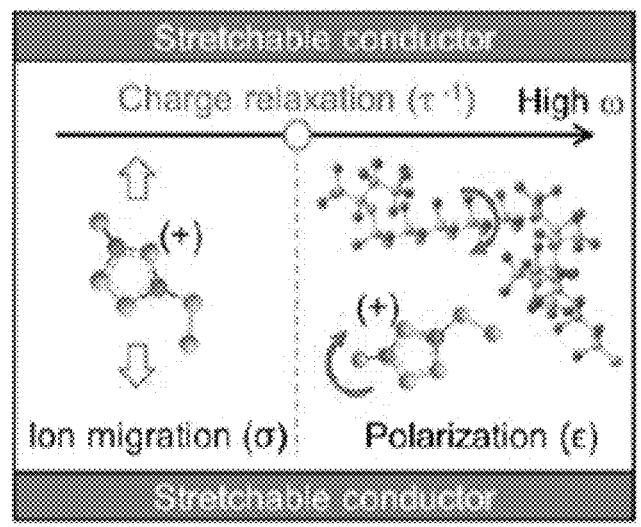
FIG. 6A schematically shows the frequency-dependent behavior of an ion conductor under an alternative electric field (alternative E-field)
Figure 6B:
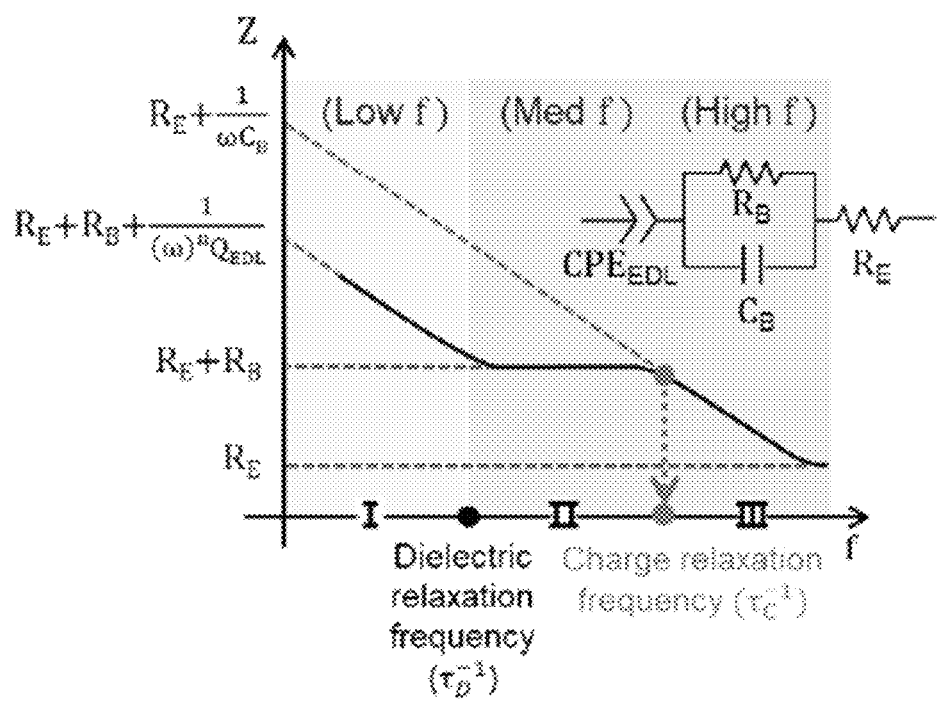
FIG. 6B shows the Bode plot of an ion conductor film.

The stretchable sensor according to the present disclosure operates based on the control of ion relaxation dynamics. In a non-Faraday ion conductor, ion migration and polarization take place under the applied AC field. The behavior of ionic molecules in a solid polymer ion conductor is described. The ion migration and polarization dominate at different times, so the electrical properties of the ion conductor depend on the measurement frequency. The ion migration having ionic conductivity σ dominates in the low-frequency range, whereas the polarization having a dielectric constant ε dominates in the high-frequency range (FIG. 6A). The ion migration and polarization determine the bulk resistance (ion resistance)

$$\left( R = \frac{1}{\sigma} \frac{c}{A} \right)$$

and bulk capacitance (geometric capacitance)

$$\left( C = \epsilon \frac{A}{d} \right)$$

along with geometric factors of area A and thickness d. The electrical behavior of the ion conductor may be analyzed using an equivalent circuit model. The Bode plot of the ion conductor shows three separate regions depending on the AC frequency, particularly a diagonal line in the low-frequency range (dominated by the electrical double layer), a flat line in the mid-frequency range (dominated by the ion migration), and a diagonal line in the high-frequency range (dominated by the molecular polarization) (FIG. 6B). In FIG. 6B, $CPE_{EDL}$ is the constant phase element of the electrical double layer, $R_B(R)$ is the bulk resistance (ion resistance), $C_B(C)$ is the bulk capacitance (geometric capacitance), and $R_E$ is the electrode resistance. R may be calculated as the real impedance in the flat region ($R \approx Z_{re}$) and C may be expressed as the imaginary impedance in the diagonal region $$\left( C \approx \frac{1}{\omega Z_{im}} \right).$$

The discharge process takes place in the RC circuit at a specific time, which may be referred to as the charge relaxation time $$\left( \tau = \frac{\epsilon}{\sigma} = RC \right)$$

Figure 6C:
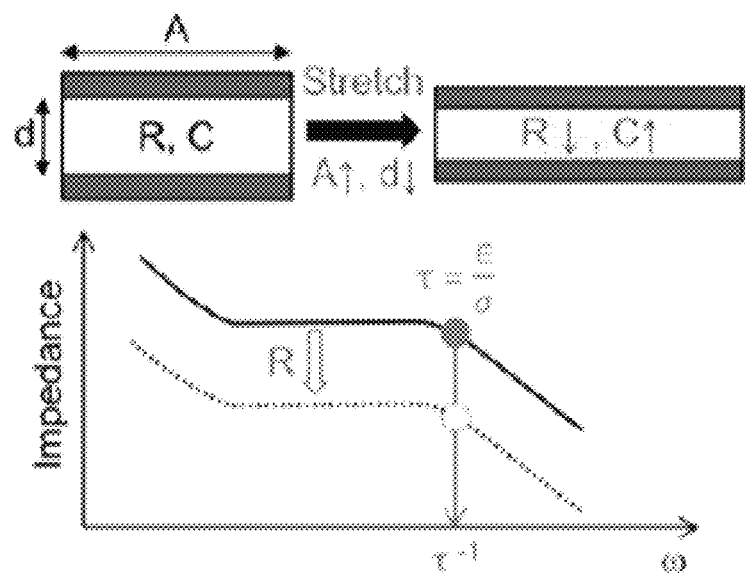
FIG. 6C is a graph showing the change of the Bode plot under mechanical stretching.
Figure 6D:
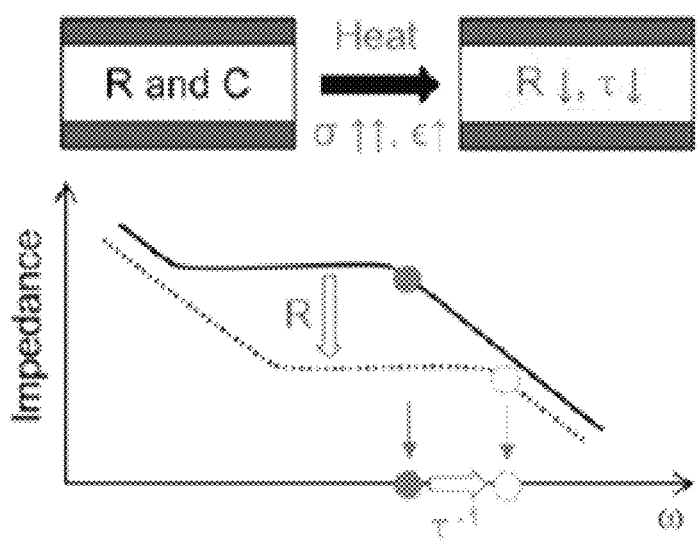
FIG. 6D is a graph showing the change of the Bode plot under thermal heating.

(different from the conductive relaxation). The charge relaxation frequency $\tau^{-1}$ is the cutoff frequency between the flat line and the high-frequency diagonal line in the Bode plot. FIG. 6C shows a change in the Bode plot under mechanical stretching. Because the impedance decreases from R and C due to stretching, the overall impedance plot shifts down, but $\tau^{-1}$, composed of the intrinsic variables (σ, ε), remains unchanged. FIG. 6D shows a change in the Bode plot under thermal heating. R decreases due to heating and $\tau^{-1}$ moves to a higher frequency. The downshift in the flat region is much greater than the downshift in the diagonal region because the temperature sensitivity is higher for ion conductivity than for the dielectric constant.

Figure 7:
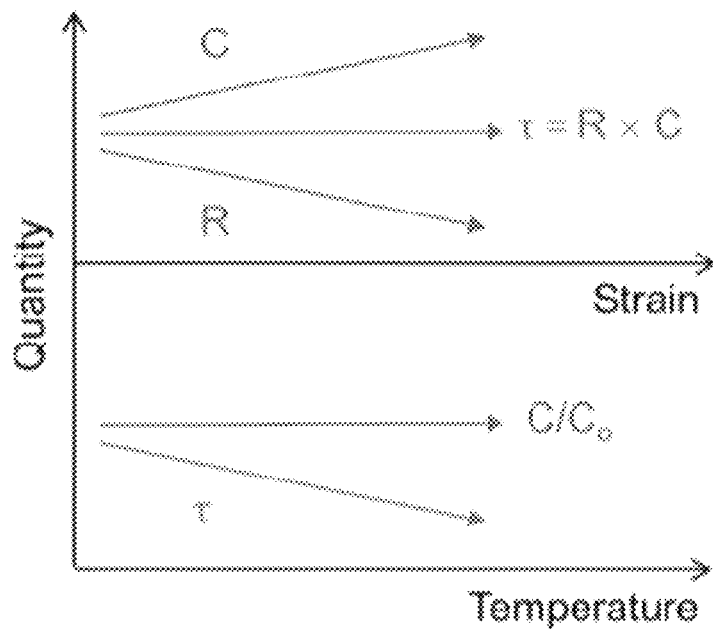
FIG. 7 is a graph showing the strain-insensitive intrinsic variable τ and the temperature-insensitive extrinsic variable $C/C_o$.

FIG. 7 is a graph showing the strain-insensitive intrinsic variable τ and the temperature-insensitive extrinsic variable $C/C_o$. With reference to FIG. 7, the relaxation time τ may be used as the strain-insensitive intrinsic variable, and is able to sense intrinsic changes such as temperature. Since ion resistance and geometric capacitance have the same dimension, the dimension parameters may be offset. Therefore, the intrinsic variable may be obtained without geometric information of the sensor. The capacitance C may be used as the temperature-insensitive extrinsic variable in order to sense the strain. The effect of temperature on the capacitance C may be eliminated through normalization by the reference capacitance $C_o$ at the measured temperature. The two variables (τ and $C/C_o$) provide complete thermo-mechanical decoupling and allow simultaneous monitoring of mechanical and thermal stimuli.

EXAMPLES

A better understanding of the present disclosure may be obtained through the following preferable examples. However, these examples are merely set forth to illustrate the present disclosure, and are not to be construed as limiting the scope of the present disclosure.

Example 1: Manufacture of Stretchable Sensor

Example 1-1

Manufacture of Bottom Layer

Figure 1A:
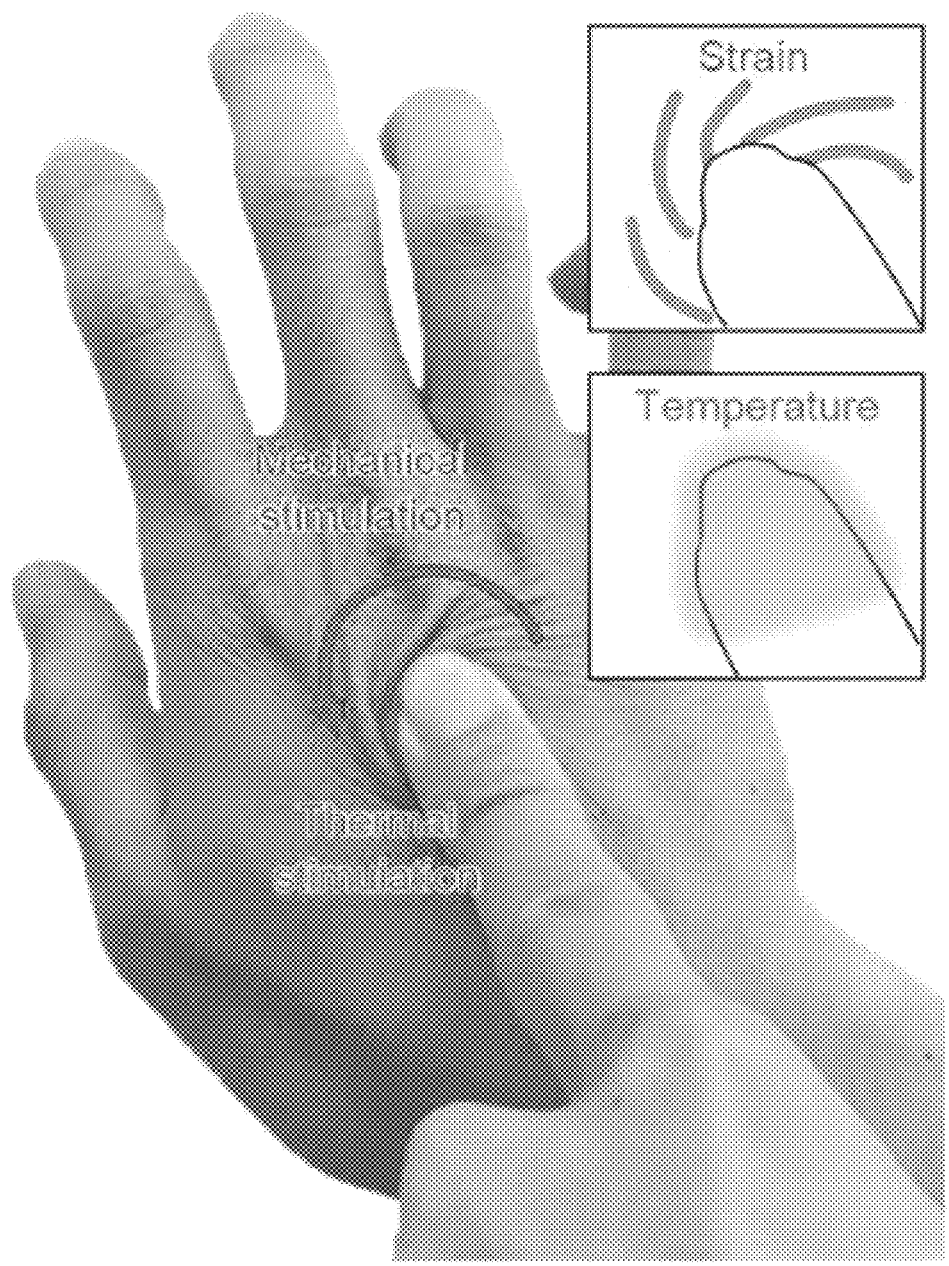
FIG. 1A shows conceptual strain and temperature profiles on actual skin when mechanical and thermal stimuli are applied simultaneously, and FIG. 1B schematically shows the actual skin including thermoreceptors and mechanoreceptors to separately recognize the tensile strain and the temperature.
Figure 1B:
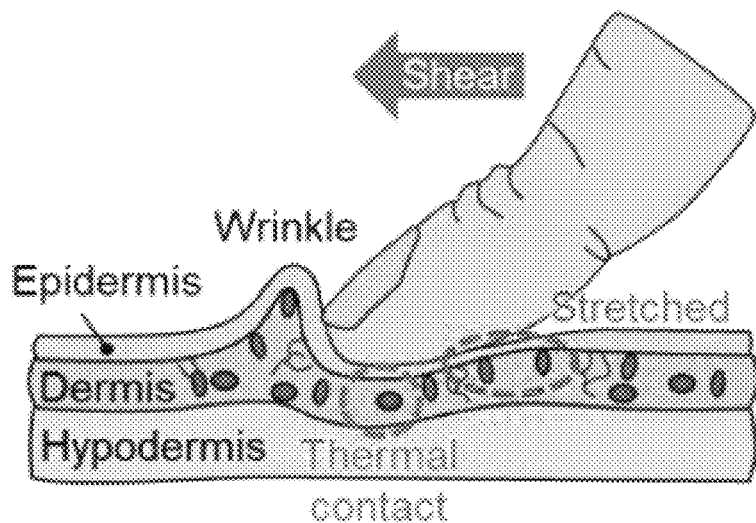

With reference to FIGS. 2 and 3, 1 g of a silver nanowire (AgNW) solution in which 1 wt % of AgNW was dispersed in isopropyl alcohol (IPA) was diluted with 19 g of IPA in a 50 ml glass vial. A stencil mask was placed on a glass slide on a hot plate at 90° C., and the diluted AgNW solution was sprayed once thereto at a rate of 45 ml/hr using a syringe pump and thus deposited. Here, the spray pressure was 0.21 Mpa, and the distance between the nozzle and the sample was 25 cm. Then, in order to remove residue, the glass slide on which AgNW was deposited was dipped in ethanol for 10 min and then taken out therefrom, and the ethanol was dried. A SEBS (poly(styrene-b-ethylene/butylene-b-styrene)) solution, obtained by dissolving 0.5 wt % of SEBS in toluene, was subjected to spin casting at 1,000 rpm for 1 min on the deposited AgNW, and the low-concentration solution penetrated between the AgNW wires of the percolated AgNW. Then, a high-concentration SEBS solution, obtained by dissolving 10 wt % of SEBS in toluene, was subjected to spin casting once more at 1,000 rpm for 1 min and then annealing at 120° C. for 30 min. Through the coating process, a stretchable electrode, which is a uniform and rigid composite film, was manufactured.

The SEBS composite was subjected to $O_2$ plasma treatment by allowing 22 sccm of $O_2$ gas to flow and applying 150 W for 30 sec. A PDMS prepolymer (a 10:1 ratio of prepolymer and curing agent) was applied through spin coating at 500 rpm for 30 sec on the $O_2$-plasma-treated SEBS film. A glass slide was placed on the PDMS to obtain a flat PDMS. The PDMS was thermally cured at 100° C. for 5 hr. The stretchable electrode thus manufactured was peeled off from the glass slide, thus manufacturing a stretchable electrode 100 including a stretchable substrate 400.

A fluoroelastomer solution, obtained by dissolving 15 wt % of e-PVDF-HFP (poly(vinylidene fluoride-co-hexafluoropropylene)) as a fluoroelastomer in a 2-butanone solvent, was applied through spin coating at 1,000 rpm for 60 sec on the surface of the AgNW of the stretchable electrode 100 including the stretchable substrate 400. The fluoroelastomer (e-PVDF-HFP) solution includes an ionic liquid in the e-PVDF-HFP solution in which 5 wt % of EMIM-TFSI (1-ethyl-3-methylimidazolium bis(trifluoromethylsulfonyl) imide) serving as the ionic liquid was dissolved. Here, the fluoroelastomer (e-PVDF-HFP) solution includes e-PVDF-HFP (0.75 g), an ionic liquid (0.0395 g), and butanone (5 g). The solvent was dried through thermal annealing at 100° C. for 1 hr, thus forming a stretchable active layer 200, thereby manufacturing a bottom layer.

Manufacture of top layer

A top layer was manufactured in the same manner as in the process of manufacturing the bottom layer described above.

Manufacture of stretchable sensor

The stretchable active layers 200 of the bottom and top layers were disposed to be in contact with each other, after which the stretchable active layers were annealed at 100° C. for 6 hr on a hot plate and thus crosslinked, thereby manufacturing a stretchable sensor 10.

Example 1-2

A stretchable sensor was manufactured in the same manner as in Example 1-1, with the exception that EMIM-TFSI, serving as the ionic liquid, was dissolved at 1 wt %, rather than being dissolved at 5 wt %, as in Example 1-1.

Example 1-3

A stretchable sensor was manufactured in the same manner as in Example 1-1, with the exception that EMIM-TFSI, serving as the ionic liquid, was dissolved at 3 wt %, rather than being dissolved at 5 wt %, as in Example 1-1.

Example 1-4

A stretchable sensor was manufactured in the same manner as in Example 1-1, with the exception that EMIM-TFSI, serving as the ionic liquid, was dissolved at 10 wt %, rather than being dissolved at 5 wt %, as in Example 1-1.

Example 1-5

A stretchable sensor was manufactured in the same manner as in Example 1-1, with the exception that EMIM-TFSI, serving as the ionic liquid, was dissolved at 20 wt %, rather than being dissolved at 5 wt %, as in Example 1-1.

Example 1-6

A stretchable sensor was manufactured in the same manner as in Example 1-1, with the exception that EMIM-TFSI, serving as the ionic liquid, was dissolved at 30 wt %, rather than being dissolved at 5 wt %, as in Example 1-1.

Example 1-7

A stretchable sensor was manufactured in the same manner as in Example 1-1, with the exception that EMIM-TFSI, serving as the ionic liquid, was dissolved at 40 wt %, rather than being dissolved at 5 wt %, as in Example 1-1.

Example 2: Ion-Electronic Skin (IE-Skin)

Figure 5A:
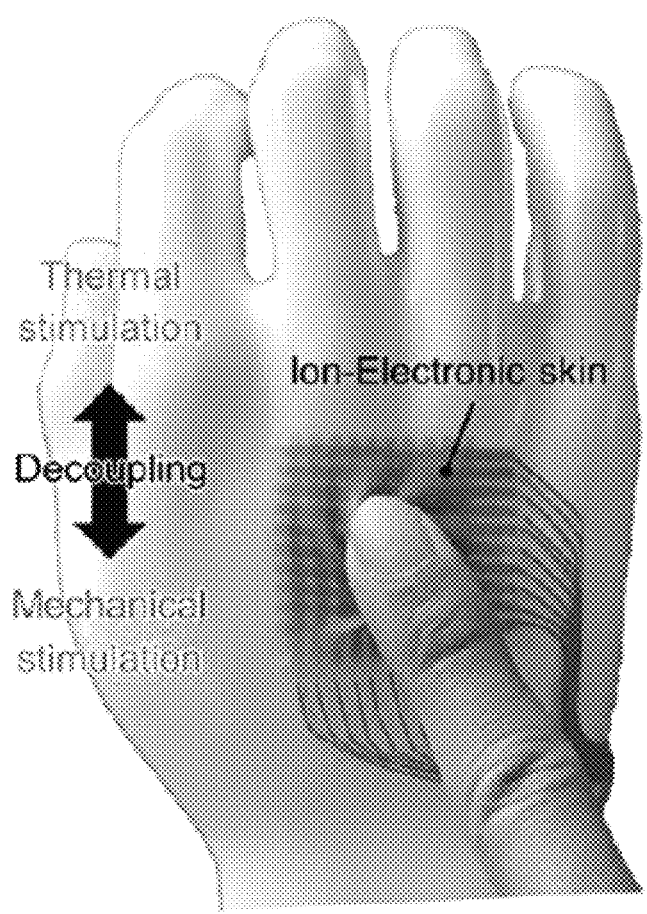
FIG. 5A shows an image of the ion-electronic skin (IE-skin) attached to a mannequin's hand, FIG. 5B schematically shows the configuration of the IE-skin, and FIG. 5C schematically shows the response of the IE-skin to shear force.
Figure 5B:
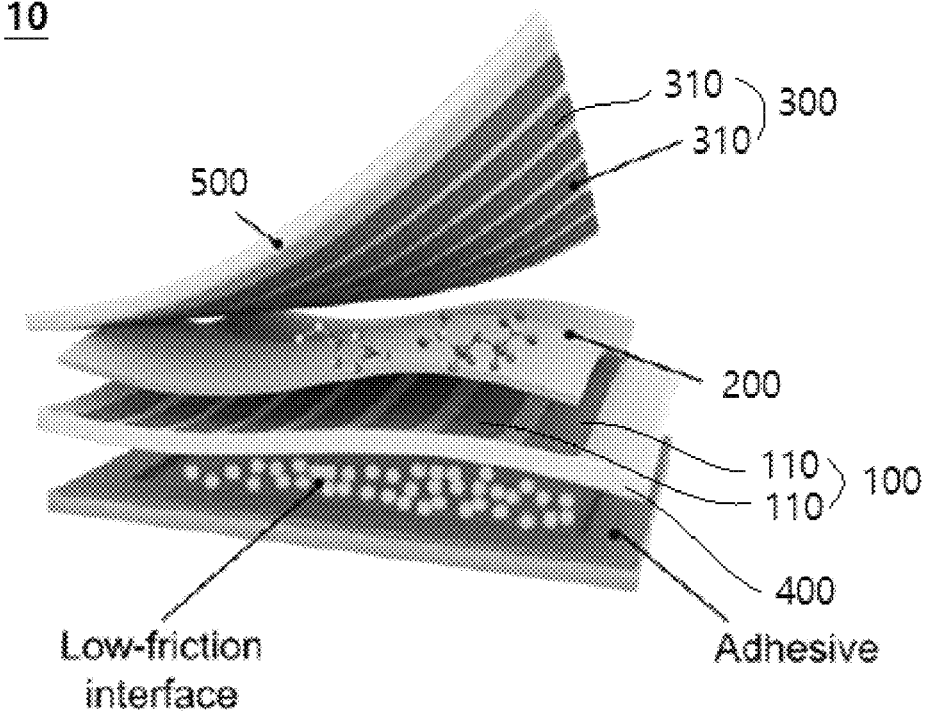

With reference to FIG. 5B, IE-skin was manufactured in the same manner as in Example 1-1, with the exception that the spray area was divided into four and spraying was performed four times in order to cover an electrode having a large area, rather than spraying the AgNW solution once, as in Example 1-1.

With reference to FIG. 5B, the IE-skin had a 10×10 matrix structure pixelated at 9 $cm^2$. The top and bottom electrodes 100, 300 had 10 line-and-space patterns of the stretchable AgNW electrode 110, 310. The line width and the space were 2 mm and 1 mm, respectively. A 5-pm-thick ion conductor film 200 containing an ion concentration of 5 wt % was interposed between the patterned electrodes 100, 300.

The spatial resolution of the pixels was determined by the pattern resolution of the stretchable electrode 100, 300.

Test Examples

Test Example 1: Analysis of Impedance

Impedance spectroscopy was performed in a thermo-hygrostat chamber using an impedance analyzer (model: PalmSense4, PalmSense, Netherlands) and an electrochemical workstation (model: Bio-Logic VMP3). The applied AC potential was 50 mV, and the frequency was scanned from 1 Hz to 1 MHz. The humidity of the chamber was maintained at 40%. The impedance was scanned several times until the temperature was stabilized after changing. Using a bespoke stretcher, the temperature response of the stretchable sensor in the stretched state was observed. For periodic and dynamic temperature measurements, the stretchable sensor was placed in a heating chamber, and the impedance was measured using an LCR meter (Agilent E4980AL).

Figure 8A:
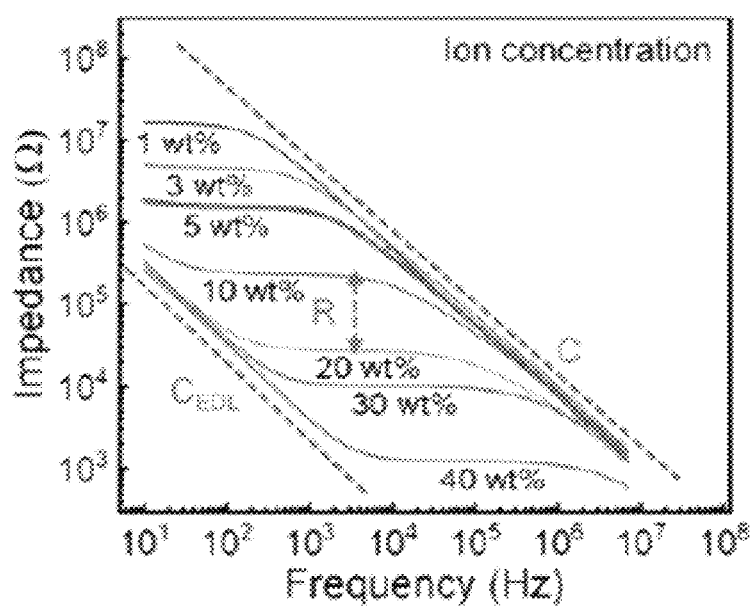
FIG. 8A shows the Bode plot of the ion conductor of each of the stretchable sensors manufactured in Examples 1-1 to 1-7 at 20° C.

FIG. 8A shows the Bode plot of the ion conductor of each of the stretchable sensors manufactured in Examples 1-1 to 1-7 at 20° C. With reference to FIG. 8A, the resistance decreased rapidly with an increase in the ion concentration, which is deemed to be due to the decreased viscosity and the increased number of mobile ions. There are three conditions for choosing an appropriate ion conductor. A low ion concentration is required to obtain high temperature sensitivity with high activation energy. Both R and C must be able to be measured at an accessible frequency ($10^2$-$10^6$ Hz). A large value of R is suitable to ensure a large impedance difference from the stretchable electrode, which is capable of suppressing the generation of noise during strain. The 5 wt % ion concentration condition was selected for the stretchable sensor.

Figure 8B:
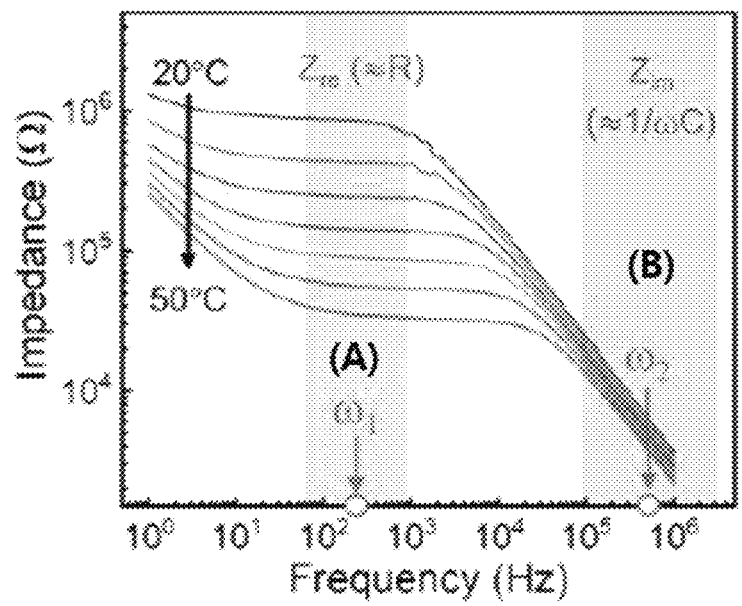
FIG. 8B shows the Bode plot of the ion conductor of the stretchable sensor manufactured in Example 1-1 at various temperatures (20° C.-50° C.)

FIG. 8B shows the Bode plot of the ion conductor of the stretchable sensor manufactured in Example 1-1 at various temperatures (20° C.-50° C.). With reference to FIG. 8B, the colored boxes represent the possible frequency range (A box) in which R values may be measured directly on all flat lines and the possible frequency range (B box) in which C values may be obtained in the diagonal region. For the stretchable sensor, R and C were measured at 200 Hz ($\omega_1$) and $5 \times 10^5$ Hz ($\omega_2$), respectively. Rather than performing the frequency sweep for each measurement, simple impedance analysis at only two frequencies is important for real-time monitoring of highly integrated IE-skin. In the ion conductor having high ion concentration ($\geq 5$ wt %), the C measurement frequency fell out of the accessible range (>$10^6$ Hz).

Figure 8C:
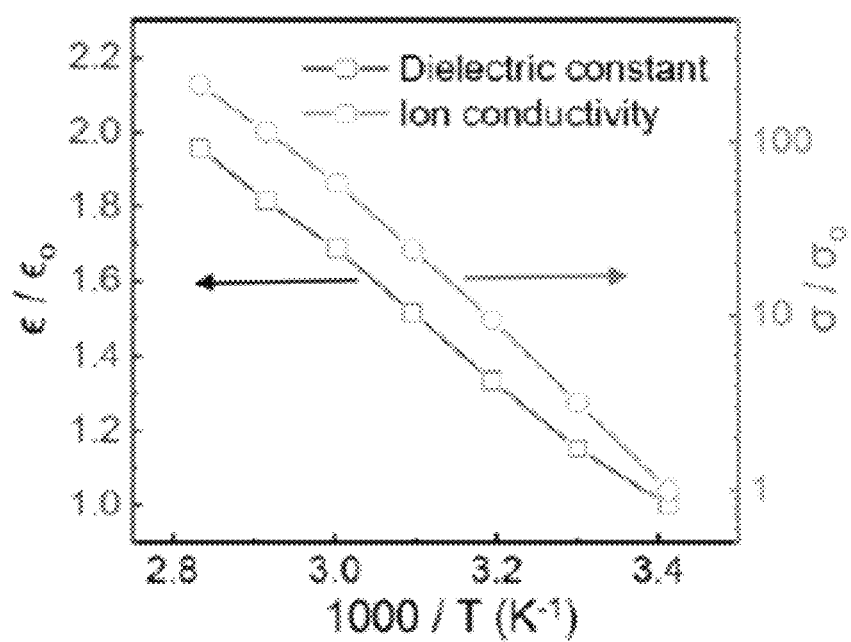
FIG. 8C is a graph showing the response of the normalized dielectric constant $\epsilon/\epsilon_0$ and the normalized conductivity $\sigma/\sigma_0$ depending on changes in temperature.

FIG. 8C is a graph showing the response of the normalized dielectric constant ($\epsilon/\epsilon_0$) and the normalized conductivity ($\sigma/\sigma_0$) depending on changes in temperature. In FIG. 8C, the x-axis, $1000/T(K^{-1})$, is the value obtained by converting the temperature (° C.) into the absolute temperature (K) and then dividing the converted value by 1,000. With reference to FIG. 8C, relative $\sigma$ was about 100 times more sensitive than relative $\epsilon$. This large difference in sensitivity is due to the fact that $\sigma$ follows Arrhenius behavior with high activation energy, whereas the change in $\epsilon$ is hardly affected by temperature change.

Test Example 2: Sensing of Strain-Insensitive Temperature of Stretchable Sensor

Figure 9A:
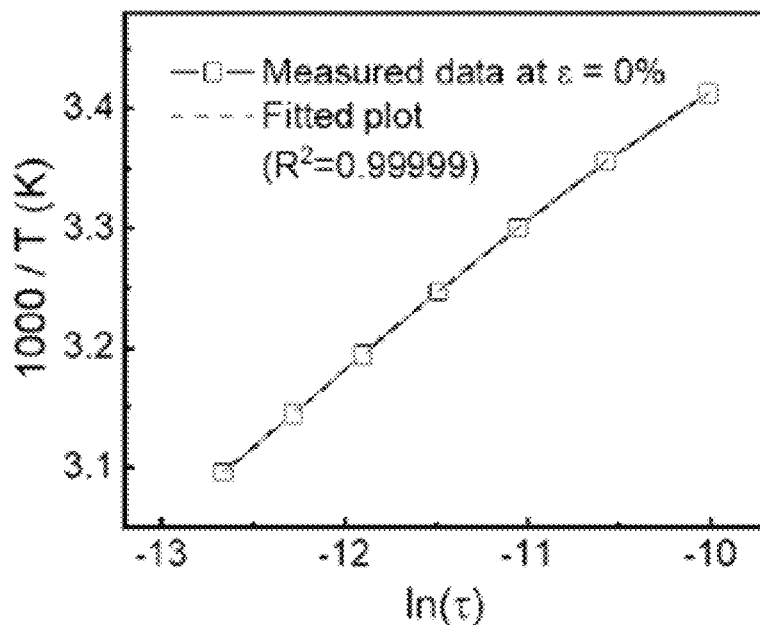
FIG. 9A shows a fitting graph of 1000/T(K) and ln(τ) to find the governing equation.
Figure 9B:
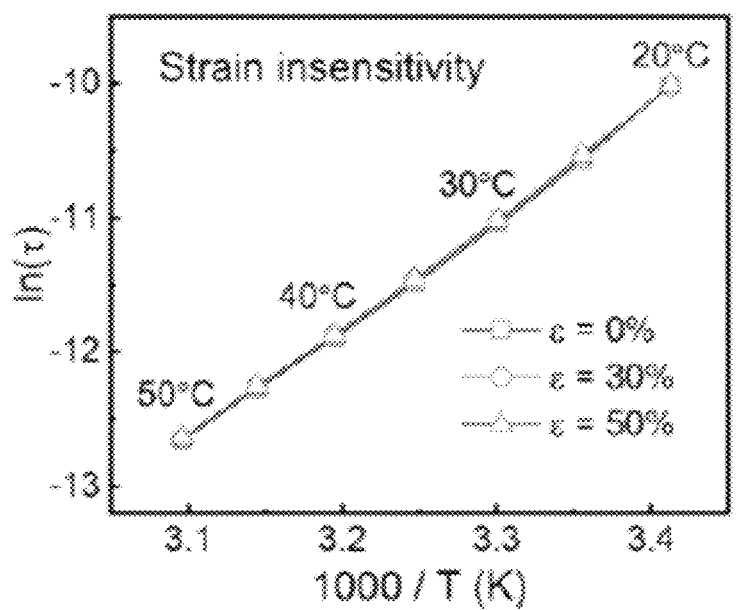
FIG. 9B is a graph showing the change in ln(τ) depending on $T^{-1}$ at three tensile strains (ε=0, 30, and 50%) of the stretchable sensor manufactured in Example 1-1.

With reference to FIG. 8B, the impedance of the stretchable sensor of Example 1-1 was measured. Here, measurement is performed at two frequencies, 200 Hz ($\omega_1$) and $5 \times 10^5$ Hz ($\omega_2$). The resistance R and the capacitance C are determined from the two measured impedance values. Briefly, the real impedance $Z_{re}$ at 200 Hz corresponds to R. C is determined from the imaginary impedance $Z_{im}$ at $5 \times 10^5$ Hz $$\left(C = \frac{1}{2\pi f \cdot Z_{im}},\right.$$

in which f=$5 \times 10^5$). The product of R and C corresponds to the relaxation time ($\tau$=RC), and the relationship between $\tau$ and temperature is determined at various temperatures. With reference to FIG. 9B, in order to make a linear equation, $\ln(\tau)$ and $1000/T(K)$ are used as the y-axis and the x-axis, respectively. Next, in order to find the governing equation, the x-axis and the y-axis are swapped and fitted. FIG. 9A is a fitting graph of $1000/T(K)$ and $\ln(\tau)$ to find the governing equation, and the governing equation is represented as Equation (3) below.

$$y = 0.0126 - 1.035x - 0.0956x^2 - 0.0026x^3 \quad (3)$$

In Equation (3), x is $\ln(\tau)$ and y is $1000/T(K)$. As such, when the value $\tau$ is determined by measuring the impedances at two frequencies using the sensor, the determined value is substituted into Equation (3), thus obtaining the temperature.

FIG. 9B is a graph showing the change in $\ln(\tau)$ depending on $T^{-1}$ at three tensile strains ($\epsilon$=0, 30, and 50%) of the stretchable sensor manufactured in Example 1-1. With reference to FIG. 9B, all plots measured at different strains ($\epsilon$=0, 30, and 50%) matched the master curve, indicating that $\tau$ is not affected by a dimension change.

The stretchable sensor manufactured in Example 1-1 was placed in a temperature control device and the temperature at 0% strain and at 50% strain was measured. The temperature was determined using $\tau$(RC) and the governing equation, and the results thereof are shown in Table 1 below.

TABLE 1

| Temp. (° C.) (Setting) | 0% strain | | | 50% strain | | | Error (° C.) (0% strain-50% strain) |
| --- | --- | --- | --- | --- | --- | --- | --- |
| | ln (RC) | 1000/T (K) | Temp. (° C.) (Calculated) | ln (RC) | 1000/T (K) | Temp. (° C.) (Calculated) | |
| 20 | −10.0108 | 3.412941 | 20.00246 | −10.0119 | 3.412839 | 20.0112 | −0.0087 |
| 25 | −10.5729 | 3.355788 | 24.99264 | −10.5337 | 3.360062 | 24.6135 | 0.37912 |
| 30 | −11.0537 | 3.300482 | 29.98609 | −11.0202 | 3.304492 | 29.6184 | 0.36767 |
| 35 | −11.491 | 3.246607 | 35.01391 | −11.458 | 3.250756 | 34.6208 | 0.39315 |
| 40 | −11.898 | 3.194587 | 40.02956 | −11.874 | 3.197677 | 39.727 | 0.30253 |

TABLE 1-continued

| | 0% strain | | | 50% strain | | | Error (° C.) |
|---|---|---|---|---|---|---|---|
| Temp. (° C.) (Setting) | ln (RC) | 1000/T (K) | Temp. (° C.) (Calculated) | ln (RC) | 1000/T (K) | Temp. (° C.) (Calculated) | (0% strain-50% strain) |
| 45 | −12.2792 | 3.145187 | 44.94613 | −12.2551 | 3.14831 | 44.6308 | 0.31536 |
| 50 | −12.6623 | 3.095799 | 50.01841 | −12.6404 | 3.098591 | 49.7273 | 0.29108 |
| | | | | | | Average | 0.291 |

As is apparent from Table 1, the average measurement error of the temperature values measured at ε=0% and at ε=50% was 0.29° C.

Figure 9C:
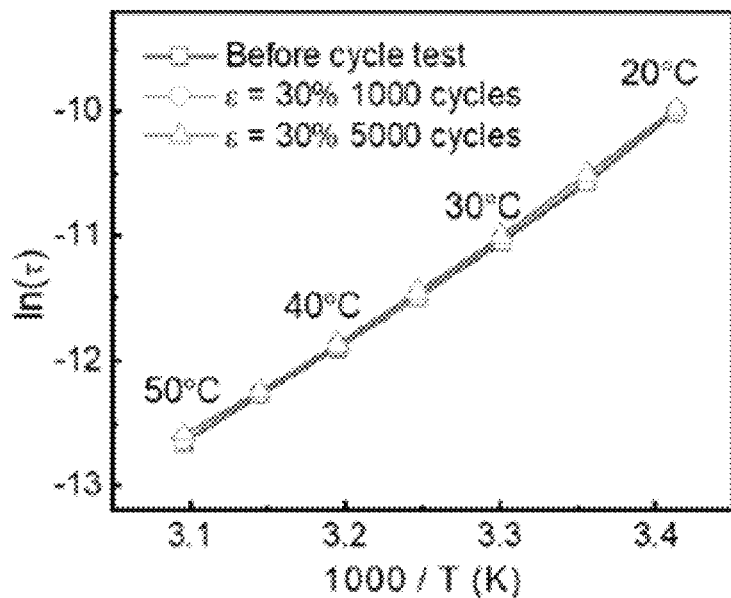
FIG. 9C is a graph showing the change of τ after 0, 1000 and 5000 cycles at 30% strain of the stretchable sensor manufactured in Example 1-1.

FIG. 9C is a graph showing the change in τ after 0, 1000 and 5000 cycles at 30% strain of the stretchable sensor manufactured in Example 1-1. With reference to FIG. 9C, at ε=30%, there was the same temperature measurement during 5000 strain cycles, and there was no thermal hysteresis phenomenon in repeated temperature cycles.

The temperature sensing by τ does not require a calibration process, thus enabling the use thereof anywhere, regardless of curvature or surface topology. Meanwhile, the intrinsically stretchable thermistor known at present needs to be calibrated when the curvature or the dimension at a location changes.

Test Example 3: Sensing of Temperature-Insensitive Strain of Stretchable Sensor

Figure 10A:
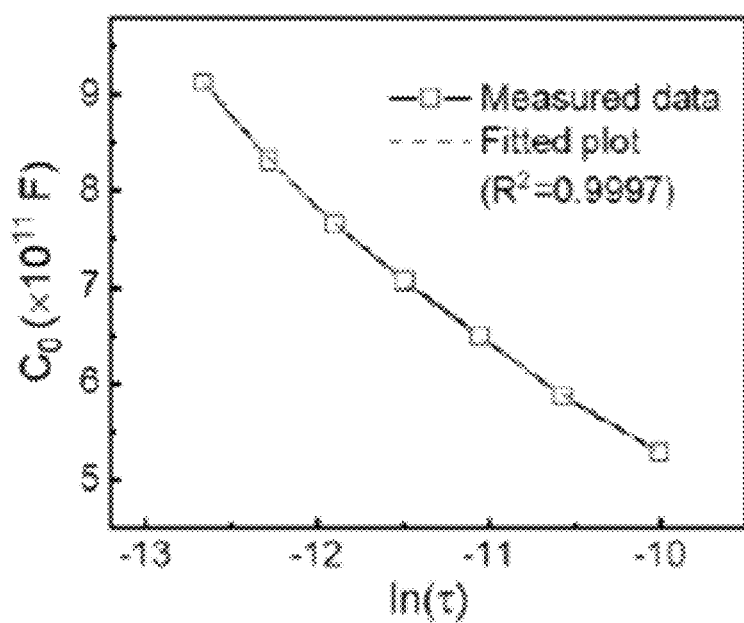
FIG. 10A shows a fitting graph of $C_o$ and ln(i) to find the governing equation.

The capacitance C is affected by both temperature and strain, so a calibration process thereof is required. First, C is measured at various temperatures in the non-stretched state (0% strain). The C value at each temperature at 0% strain is called $C_o$. Since there is a correlation between $C_o$ and temperature and there is a correlation between temperature and τ, there is a correlation between $C_o$ and τ. $C_o$ is plotted depending on τ, and thus the governing equation is determined. FIG. 10A is a fitting graph of $C_o$ and ln(τ) to find the governing equation, and the governing equation is represented as Equation (4) below.

$$y=(10^{-10})(-6.426-1.848x-0.172x^2-0.0057x^3) \quad (4)$$

In Equation (4), x is ln(τ) and y is $C_o$.

Figure 10B:
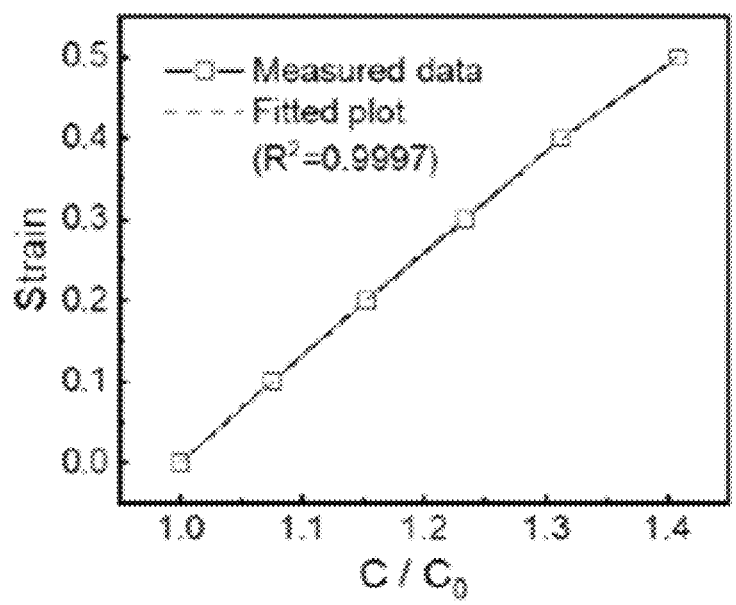
FIG. 10B shows a fitting graph of strain and $C/C_o$ to find the governing equation.

Since ln(τ) was already obtained when determining the temperature, it may be substituted into Equation (4) to obtain the $C_o$ value. When the C value is normalized to $C_o$ in the state in which the temperature and strain applied to the sensor are not known, the change due to the temperature may be calibrated. The $C/C_o$ value is a variable that responds only to strain. The strain value may be measured by plotting the $C/C_o$ value and the strain and determining the governing equation. FIG. 10B is a fitting graph of strain and $C/C_o$ to find the governing equation, and the governing equation is represented as Equation (5) below.

$$y=-0.137-1.96x+3.05x^2-0.947x^3 \quad (5)$$

In Equation (5), x is $C/C_o$ and y is strain.

Figure 10C:
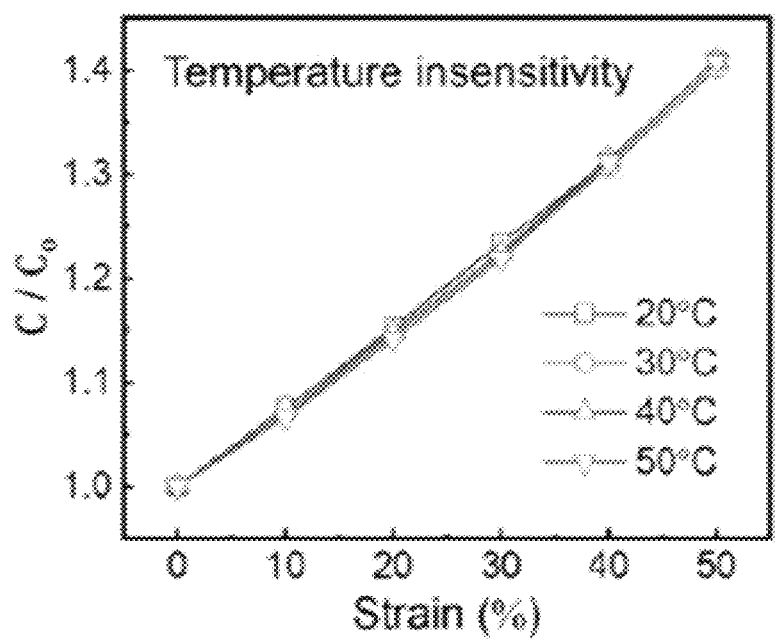
FIG. 10C is a graph showing the change of $C/C_o$ depending on the tensile strain at different temperatures of the stretchable sensor manufactured in Example 1-1.

FIG. 10C is a graph showing the change in $C/C_o$ depending on the tensile strain at different temperatures of the stretchable sensor manufactured in Example 1-1. With reference to FIG. 10C, the plot of $C/C_o$ versus uniaxial strain at various temperatures matches the master curve, so the strain may be calculated from the curve-fitting equation.

Figure 10D:
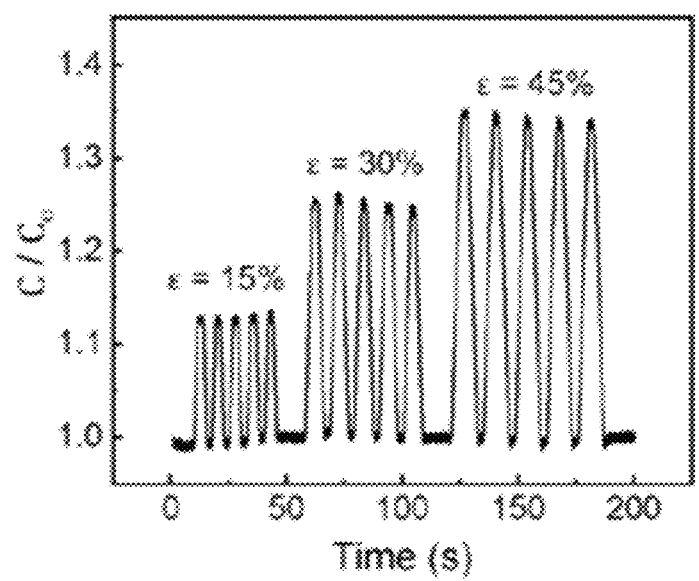
FIG. 10D is a graph showing the response of $C/C_o$ during repeated stretching cycles at different tensile strains of the stretchable sensor manufactured in Example 1-1.

FIG. 10D is a graph showing the response of $C/C_o$ during repeated stretching cycles at different tensile strains of the stretchable sensor manufactured in Example 1-1. With reference to FIG. 10D, it was confirmed that the response of $C/C_o$ during repeated stretching cycles at different strains was quantitatively distinguishable.

The stretchable sensor manufactured in Example 1-1 was placed in a strain control device, and the strain was measured at 20° C. and 50° C. The temperature was calculated using $C/C_o$ and the governing equation, and the results thereof are shown in Table 2 below.

TABLE 2

| | 20° C. | | 50° C. | | |
|---|---|---|---|---|---|
| Strain (%) (Setting) | $C/C_o$ | Strain (%) (Calculated) | $C/C_o$ | Strain (%) (Calculated) | Error (%) (20° C.-50° C.) |
| 0 | 1.000 | 0.6 | 1.000 | 0.7 | 0.1 |
| 30 | 1.231 | 30.5 | 1.224 | 29.7 | 0.8 |
| 50 | 1.428 | 52.2 | 1.416 | 51.5 | 0.7 |

As is apparent from Table 2, at 30% and 50% strain, the errors due to temperature changes at 20° C. and 50° C. were 0.8% and 0.7%, respectively.

Test Example 4: Measurement of Temperature Upon Attachment to Skin

Figure 11A:
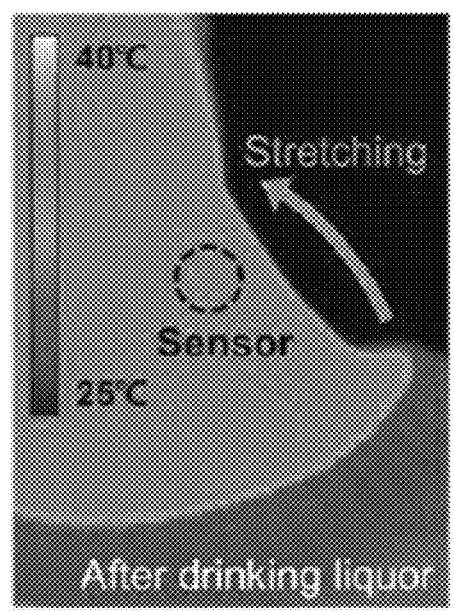
FIG. 11A shows an infrared camera image of the stretchable sensor manufactured in Example 1-1 attached to the skin over the jugular vein.

FIG. 11A shows an infrared camera image of the stretchable sensor manufactured in Example 1-1 attached to the skin over the jugular vein. With reference to FIG. 11A, the stretchable sensor was attached to the skin over the jugular vein and the body temperature was monitored before and after drinking liquor. The temperature was measured in the normal state and in the fully stretched state by tilting the neck.

Figure 11B:
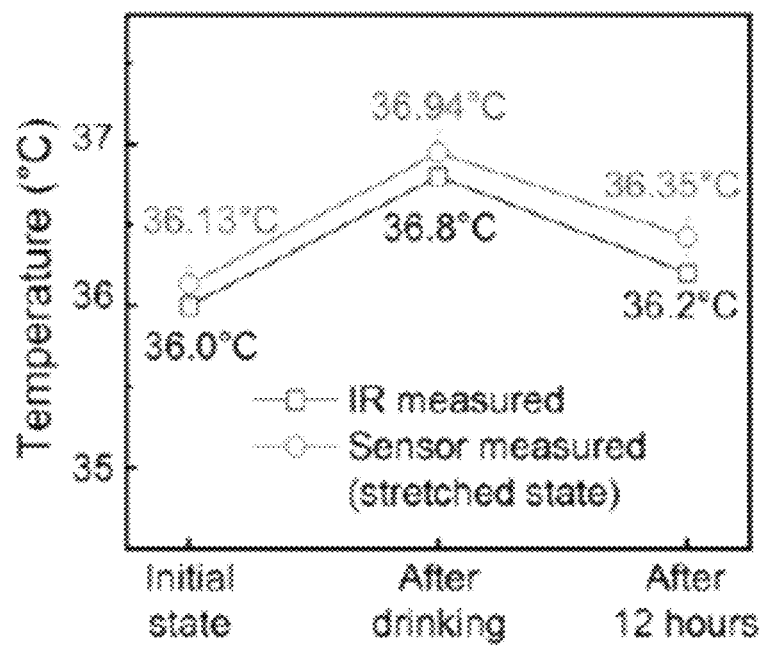
FIG. 11B is a graph showing changes in the temperature before and after drinking liquor in the stretched state of the stretchable sensor manufactured in Example 1-1 attached to the skin over the jugular vein.

FIG. 11B is a graph showing changes in the temperature before and after drinking liquor in the stretched state of the stretchable sensor manufactured in Example 1-1 attached to the skin over the jugular vein. With reference to FIG. 11B, the temperature measured using the sensor increased from 36.13° C. to 36.94° C. after drinking, and then decreased to 36.35° C. after 12 hr, which was consistent with the value measured using an IR thermometer.

Figure 11C:
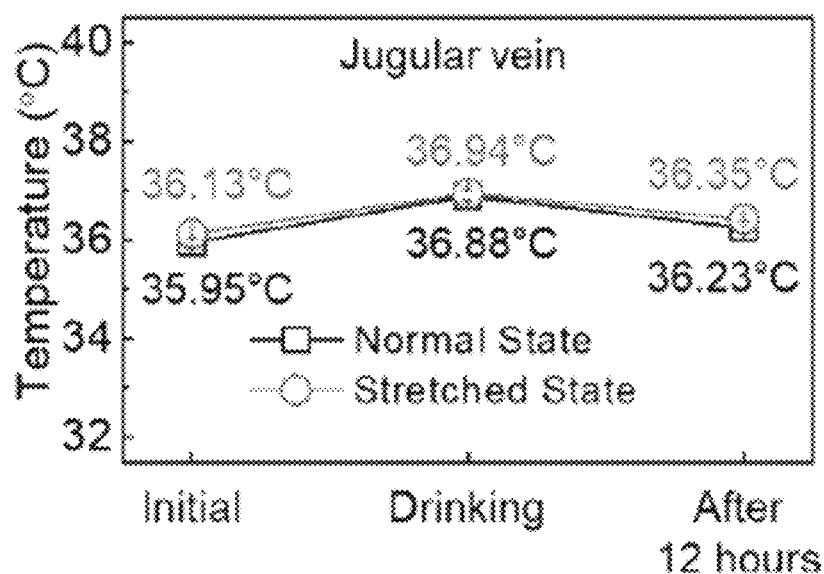
FIG. 11C is a graph showing changes in the temperature before and after drinking liquor in the normal state and in the stretched state of the stretchable sensor manufactured in Example 1-1 attached to the skin over the jugular vein.

FIG. 11C is a graph showing changes in the temperature before and after drinking liquor in the normal state and the stretched state of the stretchable sensor manufactured in Example 1-1 attached to the skin over the jugular vein. With reference to FIG. 11C, the temperature measured in the normal state and in the stretched state showed a small difference (~0.12° C.) therebetween.

Test Example 5: Confirmation of Thermo-Mechanical Decoupling

Figure 12A:
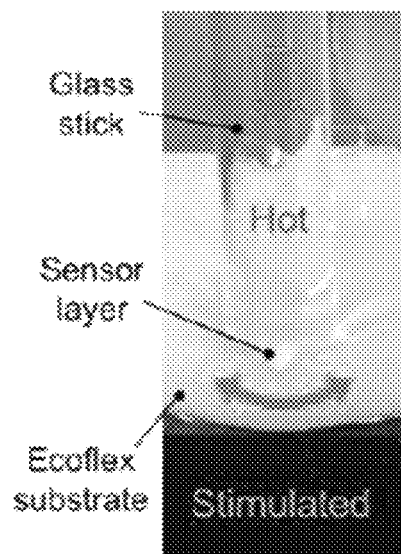
FIG. 12A shows an image when the stretchable sensor manufactured in Example 1-1 located on an elastomer (Ecoflex) substrate is pressed with a hot glass rod.
Figure 12B:
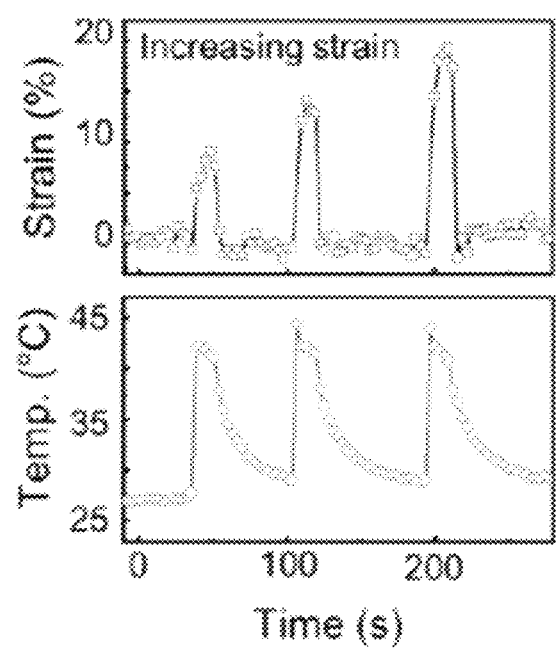
FIG. 12B is graphs showing changes in strain and temperature in FIG. 12A.

In order to confirm thermo-mechanical decoupling upon contact (pressure), a high-temperature (45° C.) glass rod was repeatedly brought into contact with the stretchable sensor manufactured in Example 1-1, placed on a thick soft elastomer substrate (Ecoflex). FIG. 12A shows an image when the stretchable sensor manufactured in Example 1-1 located on an elastomer (Ecoflex) substrate is pressed with a hot glass rod. The applied force was changed (0.4, 0.8, and 1.2 N), and the corresponding strain of the sensor was measured, and the results thereof are shown in FIG. 12B. With reference to FIG. 12B, respective strains of the sensor were 8.6%, 13.9%, and 19.1%, and the measured temperature showed the same response to contact despite the different strains of the sensor.

Test Example 6: Sensing of Unidirectional Shear

Figure 5C:
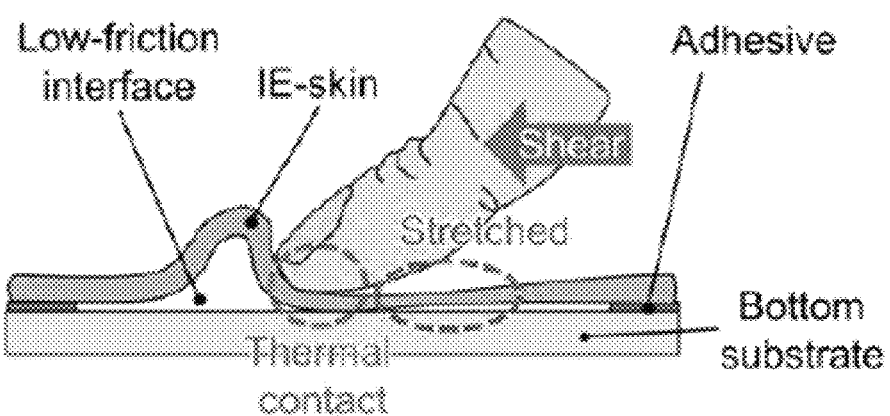

With reference to FIG. 5A, in order to perform a unidirectional shear-sensing experiment, the IE-skin manufactured in Example 2 was placed on a mannequin's hand. With reference to FIGS. 5B and 5C, rather than using the elastomer substrate that mimics the thick skin, in order to realize 3D deformation, the behavior of thin skin was mimicked by interposing a low-friction interface between the IE-skin and the bottom elastomer substrate. The interface was created by rubbing the center of the bottom substrate with excess silica particle powder (or baby powder). The edge of the IE-skin and the bottom substrate were bonded with a silicone adhesive (Sil-Poxy, Smooth-On). The contact point may be recognized by the temperature profile of the IE-skin. When shear stress is applied to the IE-skin, the front of the contact point wrinkles, and the rear of the contact point stretches.

A method of measuring the temperature and strain on IE-skin having the 10×10 matrix structure is described below.

First, the electrodes of the IE-skin are connected to a measurement device (LCR meter connected to multiple channels). The impedance is scanned at a frequency of 200 Hz to obtain the R value of each pixel in the entire 10×10 matrix. The impedance is scanned at a frequency of 5×10$^5$ Hz to obtain the C value. The temperature may be determined using the R and C values and Equation (3). The $C_o$ value may be determined using Equation (4). The strain may be determined using Equation (5). Here, the temperature value and the strain value contain errors due to the interference between pixels. The qualitative changes are observable, but absolute values are inaccurate. The corresponding values are mapped in 2D. By projecting the maximum value in the temperature profile to the strain profile, relative positions are compared, and thus various motions may be inferred.

Figure 13A:
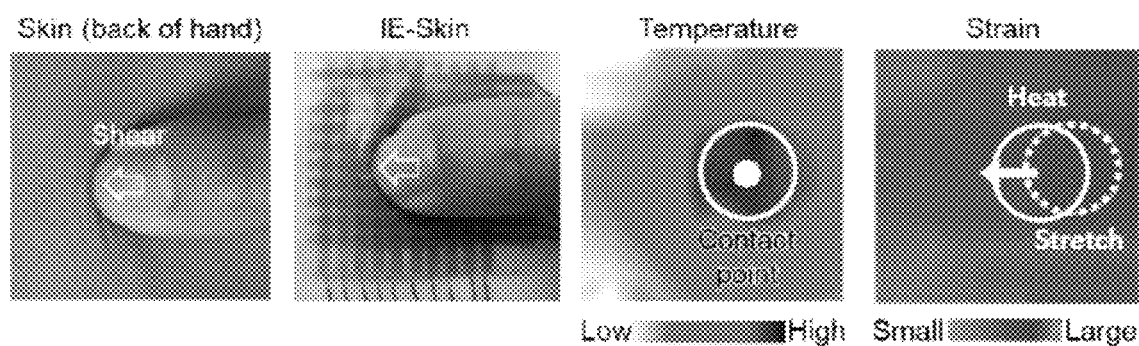
FIGS. 13A and 13B show images of the actual skin, IE-skin, 2D temperature profile and 2D strain profile when weak unidirectional shear and strong unidirectional shear are respectively applied with the index finger.
Figure 13B:
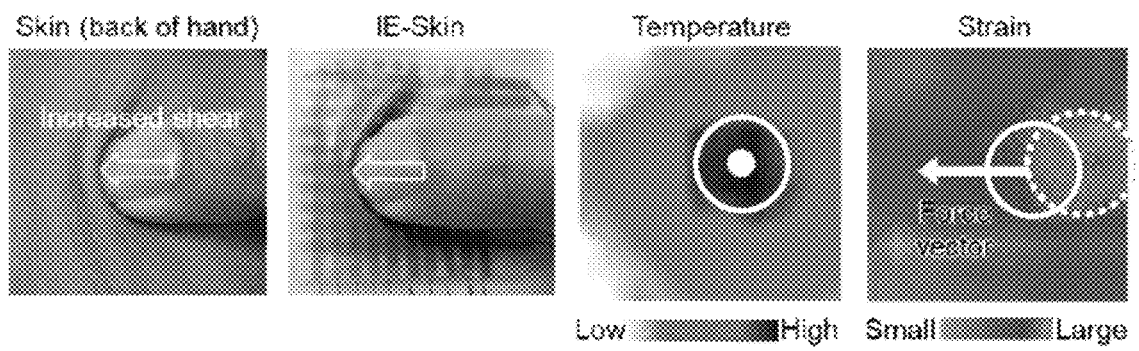

FIGS. 13A and 13B show images of the actual skin, IE-skin, 2D temperature profile and 2D strain profile when weak unidirectional shear and strong unidirectional shear are respectively applied with the index finger. The temperature and strain profiles were obtained from τ and C/$C_o$. In FIGS. 13A and 13B, the hollow white arrow represents the shear direction, and wrinkles were observed on the IE-skin as on actual skin. The contact region was identified as the highest temperature region (represented by the white circle) in the temperature profile, and the center thereof was represented by a white dot. The projection of the contact region in the strain profile shows that the stretched region (represented by the white dashed circle) is located behind the contact region in the shear direction. With reference to FIGS. 13A and 13B, as shear force increased, the strain profile was prominent in the stretched region, and the temperature profile did not show any noticeable change.

Figure 13C:
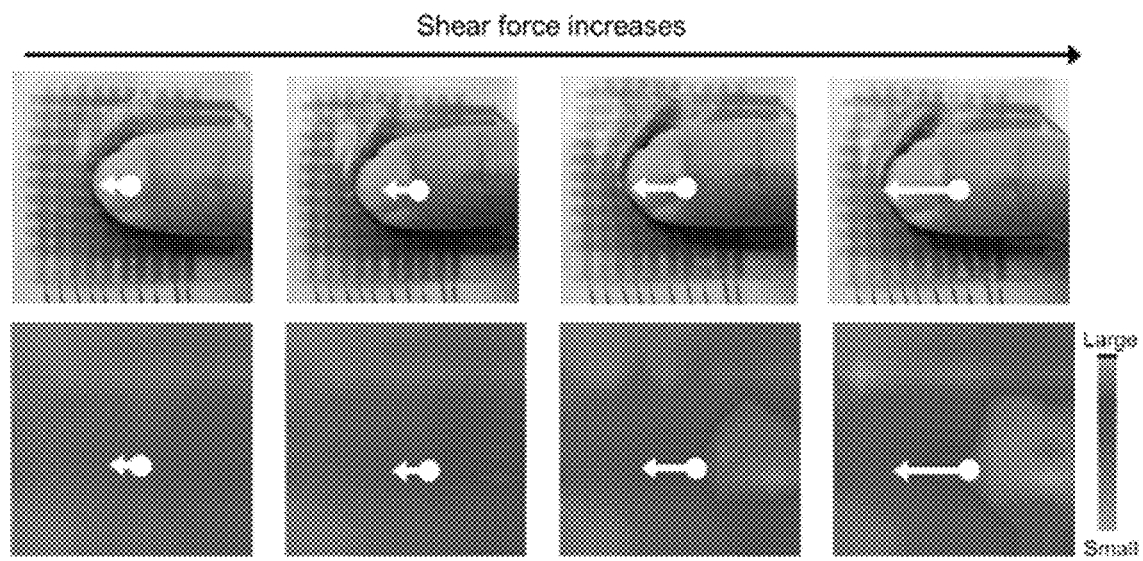
FIG. 13C shows camera images and strain profiles when shear force is applied to the IE-skin manufactured in Example 2.

FIG. 13C shows camera images and strain profiles when shear force is applied to the IE-skin manufactured in Example 2. With reference to FIG. 13C, the compression strain was relieved due to 3D wrinkle formation, based on which the shear direction can be analyzed to be a direction ranging from the stretched region to the contact region (represented by the filled white arrow). Thus, any unidirectional shear can be recognized by the force vector.

Figure 13D:
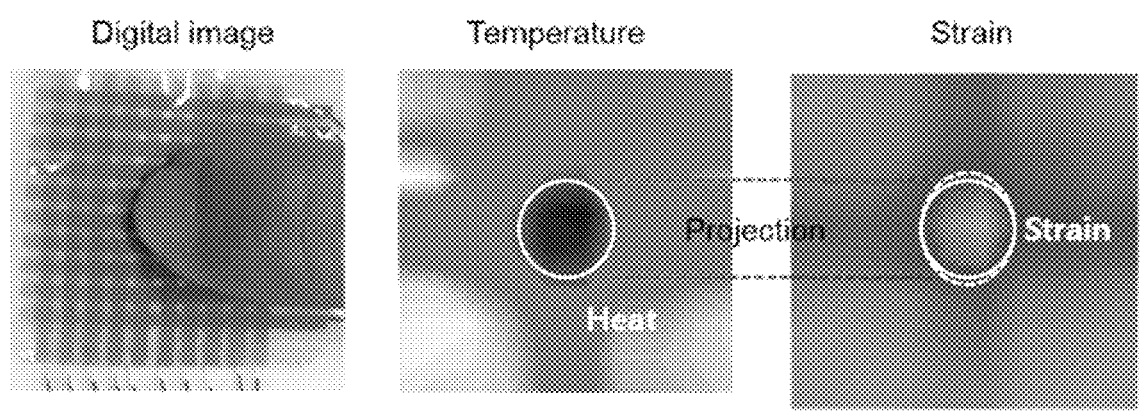
FIG. 13D shows a digital image, a temperature profile, and a strain profile when contact pressure is applied to the IE-skin manufactured in Example 2.

FIG. 13D shows the digital image, temperature profile and strain profile when contact pressure is applied to the IE-skin manufactured in Example 2. With reference to FIG. 13D, when normal force (pressure) was applied to the IE-skin, it was confirmed that the centers of the heated region and the strained region overlapped.

Test Example 7: Sensing of Multiple Shearing Motions

Figure 14A:
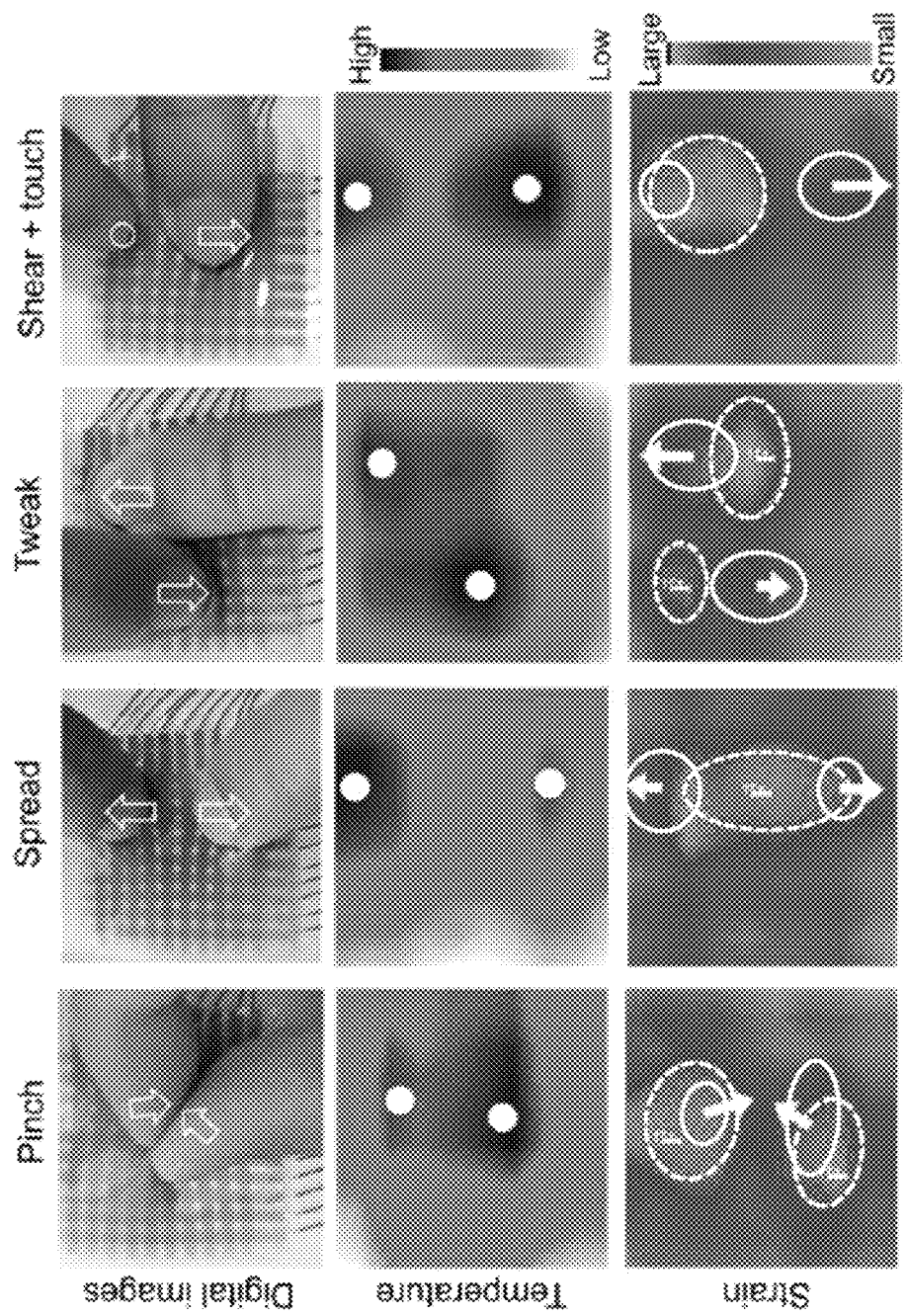
FIG. 14A shows digital images, temperature profiles and strain profiles of IE-skin by individual motions (pinch, spread, tweak, and shear & touch)

In order to sense various multiple shearing motions, pinching, spreading, tweaking, shearing, and touching were performed. The digital images, temperature profiles and strain profiles of the IE-skin by individual motions are shown in FIG. 14A. In the strain profile, the contact region obtained from the temperature profile is represented by the white circle, and the shear direction is represented by the white arrow.

With reference to FIG. 14A, the pinching motion had two shear directions at an angle of ~150°. The spreading motion had opposite shear directions on the same line, and the strain was distributed between the contact regions. The tweaking motion showed opposite shear directions next to each other. When the shear motion was combined with the touch motion, the shear direction and the touch were detected together. The recognition of additional contact in the fully stretched region implies that temperature sensing plays an important role in touch recognition by actual skin. In the shear motion, the number of contact regions is equal to or greater than the number of stretched regions.

Figure 14B:
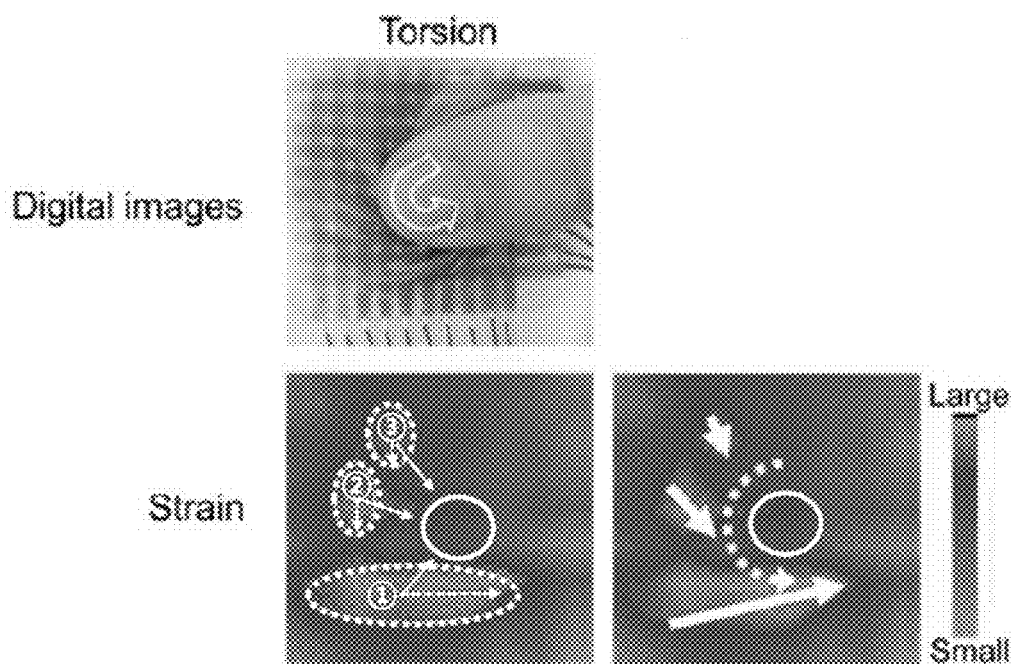
FIG. 14B shows images and strain profiles of IE-skin due to counterclockwise torsion.

The torsion motion creates more complex strain fields, thus forming complex wrinkles. The image and strain profile of the IE-skin due to the counterclockwise torsion are shown in FIG. 14B. The contact region from the temperature profile was projected to the strain profile. With reference to FIG. 14B, multiple strain regions were marked as ①, ②, and ③, and the largest ① strain region and the smallest ③ strain region were formed in the front and rear of the torsion angle, respectively. The thin white dashed arrow represents the local strain direction, and is combined with the thin white arrow representing the shear direction from the center of the strain region to the contact point. The thick white arrow is a local torsion vector, calculated as the sum of the local strain vector and the local shear vector. The local torsion vector represents the relative magnitude depending on the torsion direction and the torsion angle.

The scope of the present disclosure is represented by the claims below rather than the aforementioned detailed description, and all of the changes or modified forms that are capable of being derived from the meaning, range, and equivalent concepts of the appended claims should be construed as being included in the scope of the present disclosure.

What is claimed is:

1. A stretchable sensor, comprising:
a first stretchable electrode comprising a first elastomer and a first conductor dispersed in the first elastomer;
a stretchable active layer formed on the first stretchable electrode and comprising a third elastomer and an ion conductor dispersed in the third elastomer; and
a second stretchable electrode formed on the stretchable active layer and comprising a second elastomer and a second conductor dispersed in the second elastomer.

2. The stretchable sensor of claim 1, wherein the stretchable active layer is electrically connected to each of the first stretchable electrode and the second stretchable electrode.

3. The stretchable sensor of claim 1, wherein all or a portion of the ion conductor comes into contact with all or a portion of the first conductor at an interface between the stretchable active layer and the first stretchable electrode, and all or a portion of the ion conductor comes into contact with all or a portion of the second conductor at an interface between the stretchable active layer and the second stretchable electrode.

4. The stretchable sensor of claim 1, wherein the stretchable sensor further comprises:

a first stretchable substrate located on the first stretchable electrode in a direction opposite a direction facing the stretchable active layer; and a second stretchable substrate located on the second stretchable electrode in a direction opposite a direction facing the stretchable active layer.

5. The stretchable sensor of claim 1, wherein the first conductor and the second conductor are same as or different from each other and each of the first conductor and the second conductor independently comprises at least one selected from the group consisting of silver (Ag), gold (Au), platinum (Pt), palladium (Pd), copper (Cu), cobalt (Co), zirconium (Zr), zinc (Zn), titanium (Ti), tin (Sn), and a conductive polymer.

6. The stretchable sensor of claim 1, wherein each of the first conductor and the second conductor has a nanowire shape.

7. The stretchable sensor of claim 1, wherein each of the first elastomer and the second elastomer is a thermoplastic elastomer.

8. The stretchable sensor of claim 1, wherein the third elastomer is a thermosetting elastomer.

9. The stretchable sensor of claim 1, wherein the stretchable active layer comprises 100 parts by weight of the third elastomer and 0.1 to 50 parts by weight of the ion conductor.

10. The stretchable sensor of claim 1, wherein the ion conductor comprises an ionic liquid.

11. The stretchable sensor of claim 10, wherein the ionic liquid comprises at least one selected from the group consisting of an aliphatic ionic liquid, an imidazolium-based ionic liquid, and a pyridinium-based ionic liquid.

12. The stretchable sensor of claim 1, wherein the first stretchable electrode comprises a plurality of first electrodes parallel to each other in a linear arrangement, the second stretchable electrode comprises a plurality of second electrodes parallel to each other in a linear arrangement, the first electrodes are located perpendicular to the second electrodes, the first electrodes and the second electrodes form a pixel structure, and the stretchable sensor is used for an electronic skin.

13. A method of sensing a temperature using a stretchable sensor comprising a stretchable active layer comprising an elastomer and an ion conductor dispersed in the elastomer, comprising:

(1) measuring respective impedances ($Z_1$ and $Z_2$) at two arbitrary frequencies ($\omega_1$ and $\omega_2$) ($\omega_1 < \omega_2$);

(2) determining a resistance (R), which is a real impedance ($Z_{re}$), from the impedance ($Z_1$);

(3) determining an imaginary impedance ($Z_{im}$) from the impedance ($Z_2$) and substituting the imaginary impedance ($Z_{im}$) into Equation 1 below to obtain a capacitance (C);

(4) substituting the resistance (R) and the capacitance (C) into Equation 2 below to obtain a relaxation time ($\tau$); and (5) determining a temperature using the relaxation time ($\tau$):

$$Z_{im} = \frac{1}{\omega_i C} \quad \text{[Equation 1]}$$

$$\tau = RC \quad \text{[Equation 2]}$$

in Equations 1 and 2, $Z_{im}$ is the imaginary impedance, $\omega$ is the frequency, i is 1 or 2, C is the capacitance, $\tau$ is the relaxation time, and R is the resistance.

14. The method of claim 13, wherein the real impedance is measured at a frequency ranging from $0.001 \times 10^3$ Hz to $1.0 \times 10^3$ Hz.

15. The method of claim 13, wherein the imaginary impedance is measured at a frequency ranging from $0.001 \times 10^7$ Hz to $1.0 \times 10^7$ Hz.

16. A method of sensing a strain using a stretchable sensor comprising a stretchable active layer comprising an elastomer and an ion conductor dispersed in the elastomer, comprising:

(1') measuring respective impedances ($Z_1$ and $Z_2$) at two arbitrary frequencies ($\omega_1$ and $\omega_2$) ($\omega_1 < \omega_2$);

(2') determining a resistance (R), which is a real impedance ($Z_{re}$), from the impedance ($Z_1$);

(3') determining an imaginary impedance ($Z_{im}$) from the impedance ($Z_2$) and substituting the imaginary impedance ($Z_{im}$) into Equation 1 below to obtain a capacitance (C);

(4') substituting the resistance (R) and the capacitance (C) into Equation 2 below to obtain a relaxation time (i);

(5') determining a capacitance ($C_0$) in a non-strained state using the relaxation time ($\tau$); and (6') determining a strain using the capacitance (C) and the capacitance ($C_0$) in the non-strained state:

$$Z_{im} = \frac{1}{\omega_i C} \quad \text{[Equation 1]}$$

$$\tau = RC \quad \text{[Equation 2]}$$

in Equations 1 and 2, $Z_{im}$ is the imaginary impedance, $\omega$ is the frequency, i is 1 or 2, C is the capacitance, $\tau$ is the relaxation time, and R is the resistance.

* * * * *